US010188637B2

(12) United States Patent
Mujumdar

(10) Patent No.: US 10,188,637 B2
(45) Date of Patent: Jan. 29, 2019

(54) GRANULATE FORMULATION OF 5-METHYL-1-PHENYL-2-(1H)-PYRIDONE AND METHOD OF MAKING THE SAME

(71) Applicant: HOFFMANN-LA ROCHE INC., Little Falls, NJ (US)

(72) Inventor: Siddharthya Krishnachandan Mujumdar, Basel (CH)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 0 days.

(21) Appl. No.: 15/472,222

(22) Filed: Mar. 28, 2017

(65) Prior Publication Data

US 2017/0281609 A1 Oct. 5, 2017

Related U.S. Application Data

(60) Provisional application No. 62/314,933, filed on Mar. 29, 2016.

(51) Int. Cl.
| | | |
|---|---|---|
| *A61K 31/44* | (2006.01) | |
| *A61K 31/4412* | (2006.01) | |
| *A61K 9/20* | (2006.01) | |
| *A61K 9/16* | (2006.01) | |
| *A61K 31/4418* | (2006.01) | |

(52) U.S. Cl.
CPC ........ *A61K 31/4412* (2013.01); *A61K 9/1611* (2013.01); *A61K 9/1635* (2013.01); *A61K 9/1652* (2013.01); *A61K 9/2009* (2013.01); *A61K 9/2027* (2013.01); *A61K 9/2054* (2013.01); *A61K 9/2077* (2013.01); *A61K 9/2095* (2013.01); *A61K 31/4418* (2013.01)

(58) Field of Classification Search
CPC .......................... A61K 31/4412; A61K 9/2009
USPC ....................................................... 514/345
See application file for complete search history.

(56) References Cited

U.S. PATENT DOCUMENTS

| | | |
|---|---|---|
| 3,974,281 A | 8/1976 | Gadekar |
| 4,042,699 A | 8/1977 | Gadekar |
| 4,052,509 A | 10/1977 | Gadekar |
| 4,753,801 A | 6/1988 | Oren et al. |
| 5,104,648 A | 4/1992 | Denton et al. |
| 5,275,823 A | 1/1994 | France et al. |
| 5,310,562 A | 5/1994 | Margolin |
| 5,518,729 A | 5/1996 | Margolin |
| 5,534,262 A | 7/1996 | Dobrotvorsky et al. |
| 5,534,551 A | 7/1996 | Page et al. |
| 5,591,766 A | 1/1997 | Bang et al. |
| 5,631,296 A | 5/1997 | Birrenbach et al. |
| 5,641,536 A | 6/1997 | Lech et al. |
| 5,681,382 A | 10/1997 | Kokubo |
| 5,716,632 A | 2/1998 | Margolin |
| 5,725,883 A | 3/1998 | Staniforth et al. |
| 5,840,769 A | 11/1998 | Kolter et al. |
| 5,861,172 A | 1/1999 | Martin et al. |
| 5,879,706 A | 3/1999 | Carter et al. |
| 6,090,822 A | 7/2000 | Margolin |
| 6,113,944 A | 9/2000 | Pathak et al. |
| 6,117,451 A | 9/2000 | Kumar |
| 6,262,072 B1 | 7/2001 | Lee |
| 6,299,904 B1 | 10/2001 | Shimizu et al. |
| 6,300,349 B1 | 10/2001 | Margolin |
| 6,328,994 B1 | 12/2001 | Shimizu et al. |
| 6,348,216 B1 | 2/2002 | Kushla et al. |
| 6,361,794 B1 | 3/2002 | Kushla et al. |
| 6,599,530 B2 | 7/2003 | Vahervuo |
| 6,599,531 B2 | 7/2003 | Kushla et al. |
| 6,761,905 B2 | 7/2004 | Yeh et al. |
| 6,852,336 B2 | 2/2005 | Hunter et al. |
| 6,866,867 B2 | 3/2005 | Staniforth et al. |
| 6,956,044 B1 | 10/2005 | Margolin |
| 7,179,486 B1 | 2/2007 | Mulye |
| 7,407,973 B2 | 8/2008 | Ozes et al. |
| 7,566,729 B1 | 7/2009 | Bradford et al. |
| 7,605,173 B2 | 10/2009 | Seth |
| 7,632,521 B2 | 12/2009 | Venkatesh et al. |
| 7,767,225 B2 | 8/2010 | Radhakrishnan et al. |
| 7,825,133 B2 | 11/2010 | Yi |
| 7,863,316 B2 | 1/2011 | Kshirsagar et al. |
| 7,867,516 B2 | 1/2011 | Kiyonaka et al. |
| 7,988,994 B2 | 8/2011 | Radhakrishnan et al. |
| 8,084,475 B2 | 12/2011 | Bradford et al. |
| 8,124,124 B2 | 2/2012 | Sherry et al. |
| 8,268,352 B2 | 9/2012 | Vaya et al. |
| 8,318,780 B2 | 11/2012 | Bradford et al. |
| 8,372,415 B2 | 2/2013 | Sun et al. |
| 8,383,150 B2 | 2/2013 | Radhakrishnan et al. |
| 8,420,674 B2 | 4/2013 | Bradford |
| 8,501,160 B2 | 8/2013 | Cailly-Dufestel et al. |

(Continued)

FOREIGN PATENT DOCUMENTS

| | | |
|---|---|---|
| CA | 2842654 A1 | 1/2013 |
| CN | 101972236 A | 2/2011 |

(Continued)

OTHER PUBLICATIONS

English Translation of CN 102846555 A, Hasohan et al. (2013).*
International Search Report and Written Opinion, International Application No. PCT/US2017/024280, dated Jul. 3, 2017.
"Jitsuyou Iyakuhin Tenkabutu", Kabushiki Gaishya Kagaku Kougyou Shya, pp. 104-113 (Mar. 5, 1974).
"Phase II Trial of Pirfenidone in Children, Adolescents, and Young Adults with Neurofibromatosis Type I and Progressive Plexiform Neurofibromas," NIH Clinical Research Studies, Protocol No. 04-C-0080 (Last Update: Feb. 28, 2009).
Additional Auxiliary Requests, Opposition Proceedings of European Patent No. 1940364, filed Nov. 10, 2016.

(Continued)

*Primary Examiner* — Kevin E Weddington
(74) *Attorney, Agent, or Firm* — Marshall, Gerstein & Borun LLP

(57) ABSTRACT

The disclosure relates to granulate formulations of pirfenidone and methods of making such formulations.

11 Claims, 23 Drawing Sheets

(56) References Cited

U.S. PATENT DOCUMENTS

| | | |
|---|---|---|
| 8,507,000 B2 | 8/2013 | Mulye |
| 8,513,261 B2 | 8/2013 | Kakuda et al. |
| 8,519,140 B2 | 8/2013 | Radhakrishnan et al. |
| 8,604,084 B2 | 12/2013 | Clarke et al. |
| 8,609,701 B2 | 12/2013 | Bradford et al. |
| 8,617,595 B2 | 12/2013 | Rigassi-Dietrich et al. |
| 8,753,679 B2 | 6/2014 | Radhakrishnan et al. |
| 8,754,109 B2 | 6/2014 | Bradford et al. |
| 8,778,398 B2 | 7/2014 | Rourke et al. |
| 8,778,947 B2 | 7/2014 | Bradford |
| 8,846,088 B2 | 9/2014 | Bertelsen et al. |
| 8,911,781 B2 | 12/2014 | Antarkar et al. |
| 8,940,329 B2 | 1/2015 | Hu et al. |
| 8,951,562 B2 | 2/2015 | Politi et al. |
| 8,969,575 B2 | 3/2015 | Gant et al. |
| 9,011,911 B2 | 4/2015 | Luftensteiner et al. |
| 9,017,722 B2 | 4/2015 | Kiyonaka et al. |
| 9,018,232 B2 | 4/2015 | Zhang |
| 9,040,483 B2 | 5/2015 | Glidden et al. |
| 9,132,132 B2 | 9/2015 | Reddy et al. |
| 9,561,217 B2 | 2/2017 | Kiyonaka et al. |
| 2003/0104066 A1 | 6/2003 | Murai et al. |
| 2004/0006091 A1 | 1/2004 | Kyle et al. |
| 2004/0044003 A1 | 3/2004 | Kyle et al. |
| 2004/0048902 A1 | 3/2004 | Kiyonaka et al. |
| 2004/0106625 A1 | 6/2004 | Kyle et al. |
| 2005/0059671 A1 | 3/2005 | Sun et al. |
| 2005/0079221 A1 | 4/2005 | Groenewoud et al. |
| 2005/0245500 A1 | 11/2005 | Roth et al. |
| 2005/0267093 A1 | 12/2005 | Lehmann-Lintz et al. |
| 2005/0271724 A1 | 12/2005 | Clark et al. |
| 2006/0128717 A1 | 6/2006 | Sun et al. |
| 2006/0147528 A1 | 7/2006 | Murpani et al. |
| 2006/0199824 A1 | 9/2006 | Sun et al. |
| 2006/0258669 A1 | 11/2006 | Kyle et al. |
| 2007/0009591 A1 | 1/2007 | Trivedi et al. |
| 2007/0054842 A1 | 3/2007 | Blatt et al. |
| 2007/0203202 A1 | 8/2007 | Robinson et al. |
| 2008/0187583 A1 | 8/2008 | Massing et al. |
| 2009/0170867 A1 | 7/2009 | Kurose |
| 2009/0170868 A1 | 7/2009 | Tafesse |
| 2009/0176796 A1 | 7/2009 | Tafesse |
| 2010/0120862 A1 | 5/2010 | Tafesse |
| 2010/0130499 A1 | 5/2010 | Tafesse |
| 2010/0137306 A1 | 6/2010 | Tafesse |
| 2010/0166861 A1 | 7/2010 | Lynch |
| 2010/0178339 A1 | 7/2010 | Koo et al. |
| 2010/0239658 A1 | 9/2010 | Majuru et al. |
| 2010/0267960 A1 | 10/2010 | Wernersbach |
| 2011/0053950 A1 | 3/2011 | Meyers et al. |
| 2011/0104276 A1 | 5/2011 | Kiyonaka et al. |
| 2011/0159094 A1 | 6/2011 | Onn et al. |
| 2011/0288134 A1 | 11/2011 | Maksumova et al. |
| 2012/0183615 A1 | 7/2012 | Kiyonaka et al. |
| 2013/0011477 A1 | 1/2013 | Parthasaradhi Reddy et al. |
| 2013/0018193 A1 | 1/2013 | Liu et al. |
| 2013/0064888 A1 | 3/2013 | Solomonovich et al. |
| 2013/0115288 A1 | 5/2013 | Kiyonaka et al. |
| 2013/0266648 A1 | 10/2013 | Koo et al. |
| 2013/0310424 A1 | 11/2013 | Surber |
| 2013/0337063 A1 | 12/2013 | Reddy et al. |
| 2014/0221434 A1 | 8/2014 | Robinson et al. |
| 2014/0234415 A1 | 8/2014 | McDermott et al. |
| 2014/0296300 A1 | 10/2014 | Armendariz Borunda et al. |
| 2015/0057324 A1 | 2/2015 | Yamasaki |
| 2015/0141503 A1 | 5/2015 | Sheu et al. |
| 2015/0209341 A1 | 7/2015 | Kiyonaka et al. |
| 2015/0224086 A1 | 8/2015 | Parthasaradhi Reddy et al. |
| 2015/0297603 A1 | 10/2015 | Narang et al. |
| 2015/0320731 A1 | 11/2015 | Koo et al. |
| 2017/0100380 A1 | 4/2017 | Kiyonaka et al. |

FOREIGN PATENT DOCUMENTS

| | | | |
|---|---|---|---|
| CN | 102846555 A * | 1/2013 | .......... 514/345 |
| CN | 102846555 A | 1/2013 | |
| CN | 102846569 A | 1/2013 | |
| CN | 103271886 A | 9/2013 | |
| EP | 01/52580 A2 | 8/1985 | |
| EP | 0173516 A2 | 3/1986 | |
| EP | 0383591 | 8/1990 | |
| EP | 0383591 A2 | 8/1990 | |
| EP | 0458861 A1 | 12/1991 | |
| EP | 0837052 A1 | 4/1998 | |
| EP | 0901787 A1 | 3/1999 | |
| EP | 1138329 A2 | 10/2001 | |
| EP | 1319409 A1 | 6/2003 | |
| EP | 1356816 A1 | 10/2003 | |
| EP | 1628648 A1 | 3/2006 | |
| EP | 1757591 A1 | 2/2007 | |
| EP | 1987814 A1 | 11/2008 | |
| EP | 2261218 A2 | 12/2010 | |
| EP | 2471520 A1 | 7/2012 | |
| EP | 2533766 A2 | 12/2012 | |
| EP | 2735306 A1 | 5/2014 | |
| WO | WO-90/09176 A1 | 8/1990 | |
| WO | WO-94/26249 A1 | 11/1994 | |
| WO | WO-96/01820 A1 | 1/1996 | |
| WO | WO-96/11210 A1 | 4/1996 | |
| WO | WO-97/10712 A1 | 3/1997 | |
| WO | WO-97/41830 A1 | 11/1997 | |
| WO | WO-99/63970 A1 | 12/1999 | |
| WO | WO-00/59500 A1 | 10/2000 | |
| WO | WO-01/66551 A2 | 9/2001 | |
| WO | WO-02/08221 A2 | 1/2002 | |
| WO | WO-02/083134 A1 | 10/2002 | |
| WO | WO-02/87549 A1 | 11/2002 | |
| WO | WO-03/045313 A2 | 6/2003 | |
| WO | WO-03/66595 A2 | 8/2003 | |
| WO | WO-03/74520 A1 | 9/2003 | |
| WO | WO-03/090720 A1 | 11/2003 | |
| WO | WO-2004/002983 A2 | 1/2004 | |
| WO | WO-2004/011441 A1 | 2/2004 | |
| WO | WO-2004/019758 A2 | 3/2004 | |
| WO | WO-2004/019863 A2 | 3/2004 | |
| WO | WO-2004/029031 A2 | 4/2004 | |
| WO | WO-2004/035549 A1 | 4/2004 | |
| WO | WO-2004/058754 A1 | 7/2004 | |
| WO | WO-2004/087126 A1 | 10/2004 | |
| WO | WO-2004/089344 A1 | 10/2004 | |
| WO | WO-2004/100944 A1 | 11/2004 | |
| WO | WO-2004/103296 A2 | 12/2004 | |
| WO | WO-2005/004763 A1 | 1/2005 | |
| WO | WO-2005/004866 A1 | 1/2005 | |
| WO | WO-2005/009987 A1 | 2/2005 | |
| WO | WO-2005/009988 A1 | 2/2005 | |
| WO | WO-2005/012287 A1 | 2/2005 | |
| WO | WO-2005/016241 A2 | 2/2005 | |
| WO | WO-2005/030753 A2 | 4/2005 | |
| WO | WO-2005/030766 A1 | 4/2005 | |
| WO | WO-2005/039598 A1 | 5/2005 | |
| WO | WO-2005/040758 A2 | 5/2005 | |
| WO | WO-2005/047256 A1 | 5/2005 | |
| WO | WO-2005/066130 A1 | 7/2005 | |
| WO | WO-2005/074899 A2 | 8/2005 | |
| WO | WO-2005/079777 A1 | 9/2005 | |
| WO | WO-2007038315 A2 | 4/2007 | |
| WO | WO-2007/069773 A1 | 6/2007 | |
| WO | WO-2007/081341 A1 | 7/2007 | |
| WO | WO-2007/143959 A2 | 12/2007 | |
| WO | WO-2008/062446 A2 | 5/2008 | |
| WO | WO-2008/077068 A1 | 6/2008 | |
| WO | WO-2008/132600 A2 | 11/2008 | |
| WO | WO-2008/133973 A1 | 11/2008 | |
| WO | WO-2009/147170 A2 | 12/2009 | |
| WO | WO-2010/35282 A1 | 4/2010 | |
| WO | WO-2010/054294 A1 | 5/2010 | |
| WO | WO-2010/135470 A1 | 11/2010 | |
| WO | WO-2010/142143 A1 | 12/2010 | |
| WO | WO-2011/069089 A1 | 6/2011 | |
| WO | WO-2011/162409 A1 | 12/2011 | |

(56) References Cited

FOREIGN PATENT DOCUMENTS

| WO | WO-2014/036487 A1 | 3/2014 |
|---|---|---|
| WO | WO-2014/115082 A1 | 7/2014 |
| WO | WO-2014/136079 A1 | 9/2014 |
| WO | WO-2014/139836 A1 | 9/2014 |
| WO | WO-2015/028875 A2 | 3/2015 |
| WO | WO-2015/040093 A1 | 3/2015 |
| WO | WO-2015/054133 A1 | 4/2015 |
| WO | WO-2016/120258 A1 | 8/2016 |

OTHER PUBLICATIONS

Azuma et al., "Double-blind, Placebo-controlled Trial of Pirfenidone in Patients with Idiopathic Pulmonary Fibrosis," Am J. Respir. Crit. Care Med. 171: 1040-47 (2005).
Brief Communication of the Patent Proprietor (Intermune), Opposition Proceedings of European Patent No. EP1940364, Aug. 25, 2015.
Cain et al., Inhabition of tumor necrosis factor and subsequent endotoxin shock by pirfenidone. Int. J. Immunopharmacol. 20: 685-95 (1998).
Combined PCT Search Report and Written Opinion, PCT/US2006/037057 (dated Apr. 23, 2007).
Decision of Rejection, Chinese patent application No. 2006/0034874. 2, dated Apr. 1, 2012.
Decision on Grant, Ukrainian patent application No. 2008 05048, dated Nov. 22, 2011.
Examination Report from corresponding New Zealand patent application No. 591443, dated Jun. 22, 2012.
Examination Report, ARIPO patent application No. AP/P/2008/004390, dated Aug. 11, 2011.
Examination Report, ARIPO patent application No. AP/P/2008/004390, dated Nov. 7, 2012.
Examination Report, Australian patent application No. 2006295440, dated Dec. 3, 2010.
Examination Report, Australian patent application No. 2011201520, dated Mar. 16, 2012.
Examination Report, Australian patent application No. 2013201986, dated May 3, 2013.
Examination Report, Australian patent application No. 2014240300, dated Nov. 21, 2014.
Examination Report, European Application No. 06815221.4, dated Dec. 9, 2011.
Examination Report, European Application No. 06815221.4, dated Oct. 25, 2010.
Examination Report, European Application No. 06815221.4, dated Sep. 26, 2012.
Examination Report, European patent application No. 11007850.8, dated Feb. 24, 2017.
Examination Report, New Zealand patent application No. 565957, dated Mar. 13, 2012.
Examination Report, New Zealand patent application No. 565957, dated Mar. 24, 2011.
Examination Report, New Zealand patent application No. 565957, dated Sep. 22, 2011.
Examination Report, New Zealand patent application No. 565957, dated Jan. 14, 2010.
Examination Report, New Zealand patent application No. 591443, dated Dec. 6, 2012.
Examination Report, New Zealand patent application No. 591443, dated Jun. 22, 2012.
Examination Report, New Zealand patent application No. 591443, dated Mar. 8, 2011.
Examination Report, New Zealand patent application No. 591443, dated May 30, 2012.
Examination Report, New Zealand patent application No. 600129, dated May 30, 2012.
Examination Report, Nicaraguan National Phase Application No. 2008-000086, dated Jan. 18, 2013 (English translation).
Examination Report, Nicaraguan National Phase Application No. 2008/0086, dated Mar. 15, 2012 (English translation).
Examination Report, Philippines Application No. 1-2008-500545 (dated Sep. 21, 2011).
Examination Report, Vietnam patent application No. 1-2008-00880, dated Aug. 12, 2010.
Extended European Search Report, European patent application No. 11007850.8, dated Feb. 22, 2012.
Final office action, Japanese Patent Application No. 2008-532431 (dated May 2013).
First Examination Report, Indian Patent Application No. 2238/DELNP/2008, dated Sep. 18, 2013.
First Office Action, Chinese Patent Application No. 200680034874.2 dated Nov. 13, 2009.
First Office Action, Chinese patent application No. 201310343368. 3, dated Aug. 21, 2014.
First office action, Chinese patent application No. 20140057564.9, dated Feb. 17, 2015.
Gahl et al., "Effect of Pirfenidone on the Pulmonary Fibrosis of Hermansky-Pudlak Syndrome," Molecular Genetics and Metabolism 76: 234-42 (2002).
Gennaro (ed.), Remington Farmacia, Tomo 2, Editorial Medica Panamericana, 19th ed. pp. 2485-2489 (1995).
Georgian Search Report for corresponding Georgian Patent Application No. 10558/01 (dated Jun. 15, 2009).
Interlocutory Decision in Opposition Proceedings, European Patent No. 1940364 dated Feb. 10, 2017.
InterMune, Dissolution Profile Comparison Study Report for Pirfenidone Capsules (2008).
International Preliminary Report on Patentability, PCT/US2006/037057 (dated Mar. 26, 2008).
Martinet et al., Exaggerated spontaneous release of platelet-derived growth factor by alveolar macrophages from patients with idiopathic pulmonary fibrosis. N. Engl. J. Med. 317: 202-9 (1987).
Nagai et al., Open-label compassionate use one year-treatment with pirfenidone to patients with chronic pulmonary fibrosis, Intern. Med. 41: 1118-23 (2002).
Notari, Biopharmaceutics and Clinical Pharmacokinetics: An Introduction, Marcel Dekker, Inc., New York and Basel, pp. 134-159 (4th ed. 1986).
Notice of Appeal, Opposition Proceedings of European Patent No. 1940364, filed Apr. 20, 2017.
Notice of Final Rejection, Korean patent application No. 10-2008-7006806, dated Dec. 23, 2013.
Notice of Final Rejection, Korean patent application No. 10-2013-7022095, dated Dec. 22, 2015.
Notice of Opposition to a European patent, European Patent No. EP1940364, Mar. 11, 2015.
Notice of Reexamination, Chinese patent application No. 200680034874. 2, dated Apr. 23, 2013.
Office Action from Colombian patent application No. 08029322, completed Apr. 2012.
Office action, Canadian patent application No. 2,620,380 (dated Apr. 18, 2011).
Office Action, Canadian patent application No. 2,620,380, dated Sep. 13, 2011.
Office action, Canadian patent application No. 2,620,380, dated Sep. 20, 2010.
Office action, Canadian patent application No. 2,762,013, dated Dec. 17, 2012.
Office Action, Japanese Patent Application No. 2008-532431 (dated Apr. 17, 2012).
Office action, Korean patent application No. 10-2008-7006806 (dated Aug. 21, 2012).
Office Action, Korean patent application No. 10-2008-7006806, dated May 21, 2013.
Office Action, Korean patent application No. 10-2014-7004496, dated Dec. 21, 2015.
Office action, Mexican Patent Application No. MX/a/2008/003882 (dated Nov. 2010).
Office action, Vietnamese patent application No. 1-2008-00880 (dated Aug. 12, 2010).

(56) References Cited

OTHER PUBLICATIONS

Official Action, Eurasian patent application No. 200800881, dated Aug. 18, 2014.
Official Action, Eurasian patent application No. 200800881, dated Feb. 7, 2011.
Official Action, Eurasian patent application No. 200800881, dated Jul. 30, 2015.
Official Action, Eurasian patent application No. 200800881, dated Mar. 4, 2012.
Official Action, Japanese patent application No. 2008-532431, dated Mar. 18, 2015.
Official Action, Japanese patent application No. 2012-180913, dated Dec. 24, 2013.
Official Action, Japanese Patent Application No. 2014-129551, dated Jun. 1, 2015.
Official Action, Ukrainian patent application No. 2008 05048, dated Aug. 21, 2010.
Official Action, Ukrainian patent application No. 201203869, dated Jan. 26, 2016.
Official Action, Ukrainian patent application No. 201203869, dated Nov. 25, 2016.
Official Action, Uzebekistan patent application No. IAP 2008 0151, dated Apr. 13, 2009.
Official Action, Uzebekistan patent application No. IAP 2008 0151, dated Feb. 2011.
Official Action, Uzebekistan patent application No. IAP 2008 0151, dated Jul. 6, 2010.
Patentability Report, Ecuadorian patent application No. SP 08-8394, dated Aug. 8, 2016.
Preliminary Non-binding Opinion of the Opposition Division, European Patent No. EP1940364, Oct. 28, 2015.
Reason for Final Rejection, Japanese patent application No. 2012-180913, dated Oct. 8, 2014.
Reexamination Decision, Chinese patent application No. 200680034874.2, dated Dec. 2, 2013.
Reexamination Notice, Chinese Patent Application No. 2006 80034874.2, dated Apr. 23, 2013.
Reply of the Patent Proprietor (Intermune) to the Notice of Opposition, European Patent No. EP1940364, Jun. 11, 2014.
Report on Deliberation Results, http://www.pmda.go.jp/english/service/pdf/Pirespa-Pirfenidone.pdf.
Response to the Opposition Division's provisional opinion (dated Oct. 28, 2015) filed Sep. 29, 2016.
Schmidt et al., Bioavailability of pirfenidone capsules following oral administration (human volunteers) (60-244-73). Affiliated Medical Research, Inc. Princeton, New Jersey (1974).
Search and Examination Report, Singapore patent application No. 200801941-6, dated Mar. 5, 2010.
Second Office Action, Chinese patent application No. 200680034874.2, dated Mar. 30, 2011.
Second Office Action, Chinese patent application No. 201310343368.3, dated Jul. 14, 2015.
Second office action, Chinese patent application No. 201410057564.9, dated Jan. 8, 2016.
Shionogi & Co., Ltd., Pirespa® Tablet 200 mg Pirfenidone Tablet, Package Insert (Version 1, Oct. 2008) and English-language translation thereof.
Singapore Written Opinion (issued by the Danish Patent Ofifce) from corresponding Singaporean Patent Application No. 200801941-6 (dated Apr. 24, 2009).
Striker et al., Mesangial cell turnover: effect of heparin and peptide growth factor. *Lab Invest.* 64: 446-56 (1991).
Subsequent Substantive Examination Report, Philippines patent application No. 1/2008/500545, dated Aug. 15, 2014.
Subsequent Substantive Examination Report, Philippines patent application No. 1/2008/500545, dated Jun. 13, 2013.
Substantive Examination Report Stage 1, Indonesian application No. W-00200701530 (dated Mar. 2011).
Third Office Action, Chinese patent application No. 201410057564.9, dated Sep. 30, 2016.
Third Party Observations in the opposition proceedings against EP 1940364 B1, filed May 13, 2016.
U.S. Office Action, U.S. Appl. No. 10/470,334, dated Aug. 22, 2006.
U.S. Office Action, U.S. Appl. No. 10/470,334, dated Feb. 20, 2009.
U.S. Office Action, U.S. Appl. No. 10/470,334, dated Jun. 26, 2008.
U.S. Office Action, U.S. Appl. No. 10/470,334, dated May 11, 2007.
U.S. Office Action, U.S. Appl. No. 10/470,334, dated Oct. 2, 2009.
U.S. Office Action, U.S. Appl. No. 12/067,712 (dated Nov. 15, 2010).
U.S. Office Action, U.S. Appl. No. 12/426,182 (dated Apr. 8, 2010).
U.S. Office Action, U.S. Appl. No. 12/426,182 (dated Nov. 18, 2009).
U.S. Office Action, U.S. Appl. No. 12/426,182 (dated Sep. 16, 2009).
U.S. Office Action, U.S. Appl. No. 12/941,994, dated Jun. 23, 2011.
U.S. Office Action, U.S. Appl. No. 13/162,048, dated Apr. 13, 2012.
U.S. Office Action, U.S. Appl. No. 13/333,142, dated Apr. 27, 2012.
U.S. Office Action, U.S. Appl. No. 13/662,221, dated Aug. 25, 2014.
U.S. Office Action, U.S. Appl. No. 13/662,221, dated Jan. 24, 2014.
U.S. Office Action, U.S. Appl. No. 13/662,221, dated Mar. 18, 2013.
U.S. Office Action, U.S. Appl. No. 14/271,720, dated Apr. 23, 2015.
U.S. Office Action, U.S. Appl. No. 13/776,079, dated May 29, 2013.
U.S. Office Action, U.S. Appl. No. 14/951,313, dated Mar. 14, 2016.
Van Barneveld et al., Natural course of bleomycin-induced pneumonitis . A follow-up study.*Am. Rev. Respir Dis.* 135: 48-51 (1987).
Zhang et al., Pirfenidone reduces firbonectin synthesis by cultured human retinal pigment epithelial cells. *Aust. N Z J. Ophthalmol.* 26: S74-6 (1998).
Canadian Patent Application No. 2,937,365, Office Action, dated Nov. 27, 2017.
Grounds of Appeal, Opposition Proceedings of European Patent No. 1940364, filed Jun. 12, 2017.
Jin et al., Factors affecting therapeutic compliance: A review from the patient's perspective, Therapeutics and Clinical Risk Management, 4(1):269-86 (2008).
Reply to Appeal, Opposition Proceedings of European Patent No. 1940364, dated Nov. 6, 2017.
European Medicines Agency, CHMP Assessment Report, Esbriet, International Nonproprietary Name: Pirfenidone, Procedure No. EMEA/H/C/002154, dated Dec. 16, 2010.
Casy et al., Opioid Analgesics Chemistry and Receptors, Springer Science+Business Media, LLC, 1986.
European Patent Application No. 11007850.8, Communication Pursuant to Article 94(3): EPC, dated Apr. 5, 2018.
U.S. Appl. No. 15/706,187, Radhakrishnan et al., "Method for Preparing a Granulate Formulation of Pirfenidone and Pharmaceutically Acceptable Excipients", filed Sep. 15, 2017.
U.S. Appl. No. 15/385,451, Nonfinal Office Action, dated Oct. 10, 2017.
U.S. Appl. No. 13/776,079, Nonfinal Office Action, dated May 29, 2013.
Canadian Patent Application No. 2937365, Office Action, dated Jul. 28, 2017.
Castro et al., Biomarkers in systemic sclerosis, Biomark. Med., 4(1):133-47 (2010).
Collard, Idiopathic pulmonary fibrosis and pirfenidone, Eur. Respir. J., 35(4):728-9 (2010).
Hancock et al., The relative densities of pharmaceutical powders, blends, dry granulations, and immediate release tablets, Pharm. Technol. 2003;27(4):64-80.
Hummers, The current state of biomarkers in systemic sclerosis, Curr. Rheumatol. Rep., 12(1):349(2010).
Pitt et al., Compression prediction accuracy from small scale compaction studies to production presses, Powder Tech. 2015;270(Part B):490-493.
Tzouvelekis et al., Serum biomarkers in interstitial lung diseases, Respir. Res., 6:78 (2005).
van den Blink et al., Serum biomarkers in idiopathic pulmonary fibrosis, Pulm Pharmacol., 23(6):515-20 (2010).
Vij et al., Peripheral blood biomarkers in idiopathic pulmonary fibrosis, Transl. Res., 159(4):218-27 (2012).

* cited by examiner

Comparative Example Formulation
(Without Intragranular Glidant)

Example 1 Formulation
(With Intragranular Glidant)

Hardness and thickness of resulting tablet cores are shown in parenthesis in Newton and millimeters, respectively.
Abbreviation: MCF = main compression force in kilo-Newton.

GRANULATE FORMULATION OF 5-METHYL-1-PHENYL-2-(1H)-PYRIDONE AND METHOD OF MAKING THE SAME

BACKGROUND

Field of the Disclosure

The disclosure relates to granulate formulations of pirfenidone and methods of making granulate formulations of pirfenidone.

Brief Description of Related Technology 5-methyl-1-phenyl-2-(1H)-pyridone (also referred to as pirfenidone) is a non-peptide synthetic molecule with a molecular weight of 185.23 daltons. Its chemical elements are expressed as $C_{12}H_{11}NO$, and its structure is known. Pirfenidone has anti-fibrotic properties via: decreased TNF-α expression, decreased PDGF expression, and decreased collagen expression.

One important use of pirfenidone is known to be providing therapeutic benefits to patients suffering from fibrosis conditions such as Hermansky-Pudlak Syndrome (HPS) associated pulmonary fibrosis and idiopathic pulmonary fibrosis (IPF). Pirfenidone demonstrates a pharmacologic ability to prevent or remove excessive scar tissue found in fibrosis associated with injured tissues including that of lungs, skin, joints, kidneys, prostate glands, and livers. Published and unpublished basic and clinical research suggests that pirfenidone may safely slow or inhibit the progressive enlargement of fibrotic lesions, remove pre-existing fibrotic lesions, and prevent formation of new fibrotic lesions following tissue injuries.

It is understood that one mechanism by which pirfenidone exerts its therapeutic effects is modulating cytokine actions. Pirfenidone is a potent inhibitor of fibrogenic cytokines and TNF-α. It is well documented that pirfenidone inhibits excessive biosynthesis or release of various fibrogenic cytokines such as TGF-β1, bFGF, PDGF, and EGF. Zhang S et al., Australian and New England Journal Ophthalmology, 26; S74-S76, 1998. Experimental reports also show that pirfenidone blocks the synthesis and release of excessive amounts of TNF-α from macrophages and other cells. Cain et al., International Journal Immunopharmacology, 20:685-695 (1998).

SUMMARY OF THE DISCLOSURE

In accordance with an embodiment of the disclosure, a granulate formulation of pirfenidone can include granules of pirfenidone and glidant and optionally one or more additional pharmaceutically acceptable excipients admixed with the granules.

In accordance with an embodiment of the disclosure, a method of making a granulate formulation of 5-methyl-1-phenyl-2-(1H)-pyridone can include mixing the 5-methyl-1-phenyl-2-(1H)-pyridone and intragranular excipients in a fluid bed granulator to form granules, wherein the granules comprise a glidant; and optionally adding one or more extragranular excipients to the granules to form the granulate formulation.

In any of the foregoing embodiments, the glidant can be included intragranularly in an amount of at least 1% by weight based on the total weight of the formulation.

In any of the foregoing embodiments, the formulation can include an intragranular glidant and an extragranular disintegrant.

In any of the foregoing embodiments, the formulation can include granules with pirfenidone, filler, binder, and glidant. The formulation can further include in some embodiments, disintegrant, lubricant, and further glidant as extragranular components added to granules.

In accordance with an embodiment of the disclosure, a tablet can comprise the formulation of any of the foregoing embodiments or embodiments disclosed herein. In accordance with other embodiments of the disclosure, the tablet can consist of the formulation of any of the foregoing embodiments or embodiments disclosed herein. In accordance with other embodiments of the disclosure, the tablet can consist essentially of the formulation of any of the foregoing embodiments or embodiments disclosed herein.

DETAILED DESCRIPTION

Pirfenidone capsules are commercially available under the tradename Esbriet®, and are provided as a size #1 267 mg capsule. For many treatment regimens, including, for example, treatment of idiopathic pulmonary fibrosis, dosage amounts of 801 mg three times per day are often prescribed, requiring a patient to take 9 capsules per day. For some patients, tablet formulations can represent a more patient friendly and compliant regimen. For example, in accordance with embodiments of the disclosure, tablets can include 801 mg of pirfenidone, allowing for administration of one tablet, three times a day, or a total of three tablets. Tablets in accordance with embodiments of the disclosure can include from 100 mg to 1200 mg of pirfenidone. For example, a dosage strength can be 200 mg, 267 mg, 534 mg, 600 mg, or 801 mg pirfenidone for a unit dose in accordance with an embodiment of the disclosure. Variations of the dosage strength can ease patient administration, for example, when dose titrating. Tablets in accordance with embodiments of the disclosure can be film coated. The film coating can be colored, for example, to distinguish between different dosage strengths.

In view of the dosage requirements, oral dosage forms of pirfenidone, and particularly tablets, generally require high concentrations of pirfenidone in order to provide a tablet size that is of a manageable size for oral administration. Pirfenidone as an active ingredient, however, has poor powder flowability characteristics, e.g. for formulation processing. In view of the high concentrations of the active ingredient needed in the dosage form, there remains little room for excipients to aid in improving the flowability and processability of pirfenidone powder. Typically, formulation processes would utilize higher concentrations of excipients, particularly with difficult to process active ingredients. Such conventional formulation techniques, however, cannot be utilized where a high concentration of active is needed. It has been discovered that the formulations disclosed herein provide a formulation that exhibits good flow properties during the granulation process, are capable of being compressed into tablets under standard compression conditions and result in stable tablets that resist cracking, yet maintain the desired dissolution properties.

Figure 3:
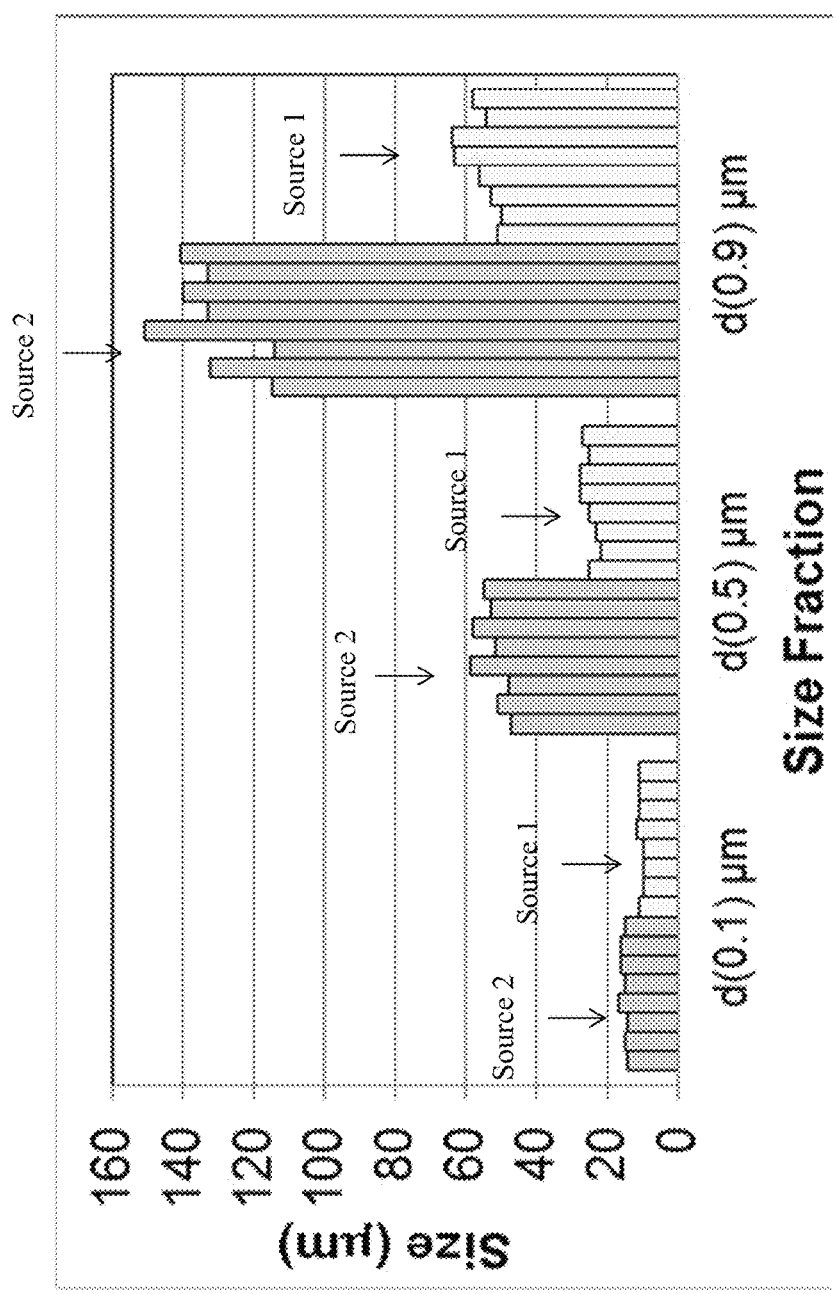
FIG. 3 is a graph illustrating the differences in particle size distribution of pirfenidone supplied from two different sources, Source 1 and Source 2.
Figure 4A:
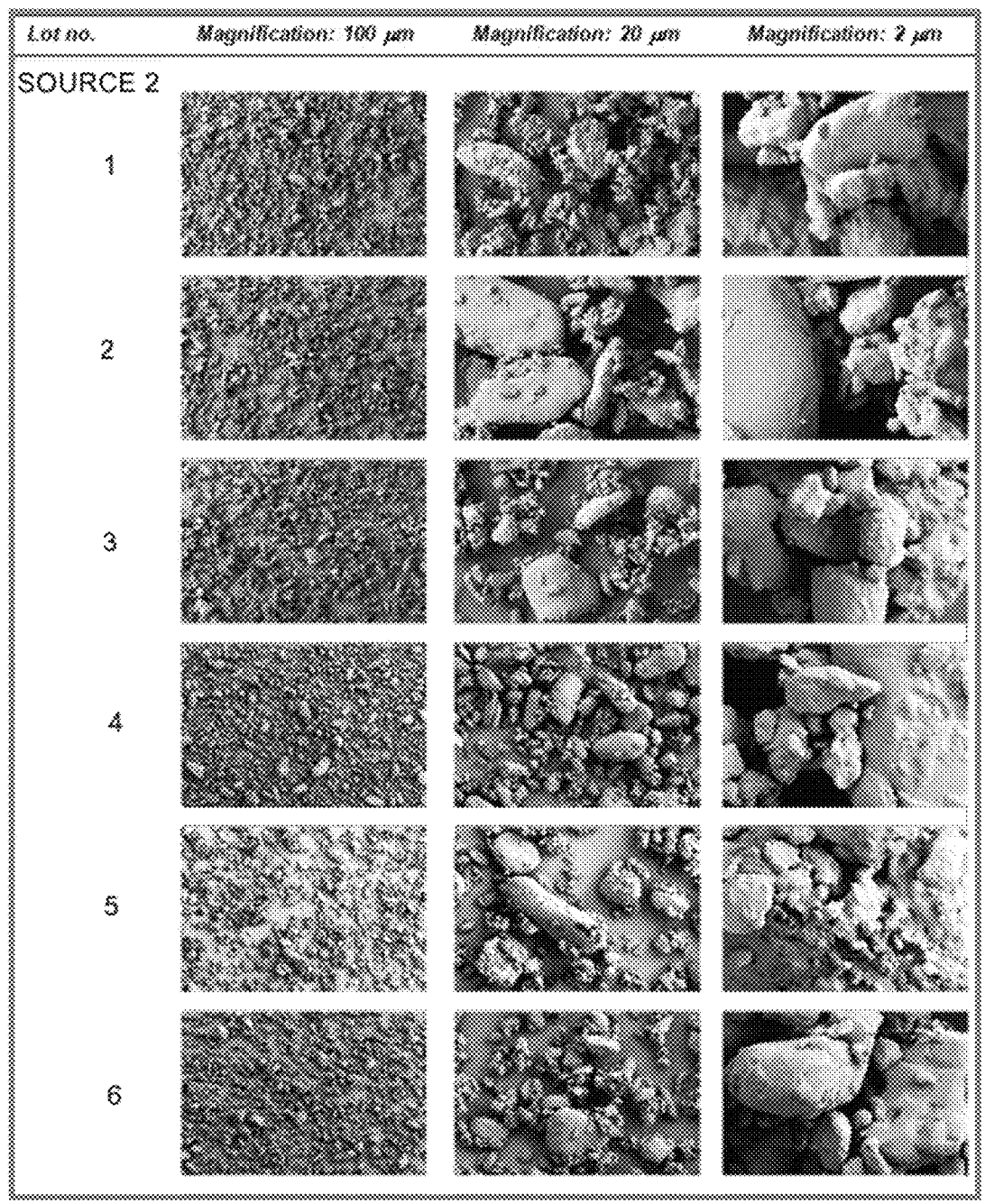
FIG. 4A is scanning electron microscope images of pirfenidone supplied from Source 2.
Figure 4B:
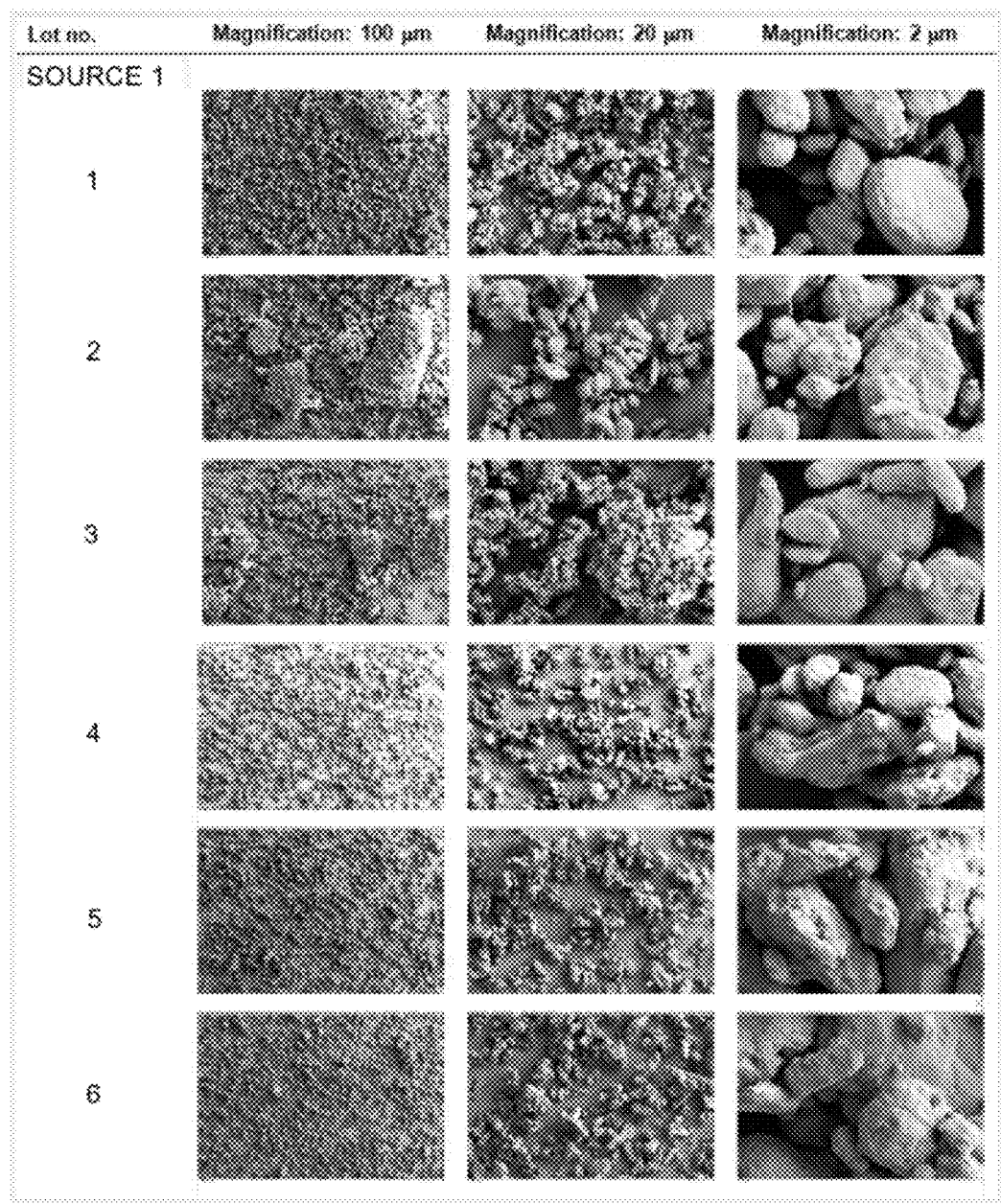
FIG. 4B is scanning electron microscope images of pirfenidone supplied from Source 1.

Pirfenidone is a highly crystalline, non-hygroscopic solid with a melting point range between 106° C. to 112° C. It has been found that the particle size of pirfenidone can vary by suppliers. Referring to FIG. 3, for example, it was found that pirfenidone from two different suppliers, Source 1 and Source 2, had distinct particle size distributions. In particular, pirfenidone from Source 1 was found to have a $d_{90}$ particle size between 50 µm to 64 µm, while pirfenidone supplied from Source 2 was found to have a $d_{90}$ particle size between 114 µm to 151 µm. FIGS. 4A and 4B are scanning electron microscopy images that further illustrate the differences in particle sizes observed with the differently sourced pirfenidone. As shown in FIGS. 4A and 4B, pirfenidone consists of irregular shaped primary particles. The shape of the primary particles is comparable between the two sources. The smaller primary particles were found to have a tendency to form agglomerates. Higher levels of agglomerates were found in Source 1 as compared to Source 2 and in some batches of Source 1 drug substance, larger-sized agglomerates were found.

Figure 5:
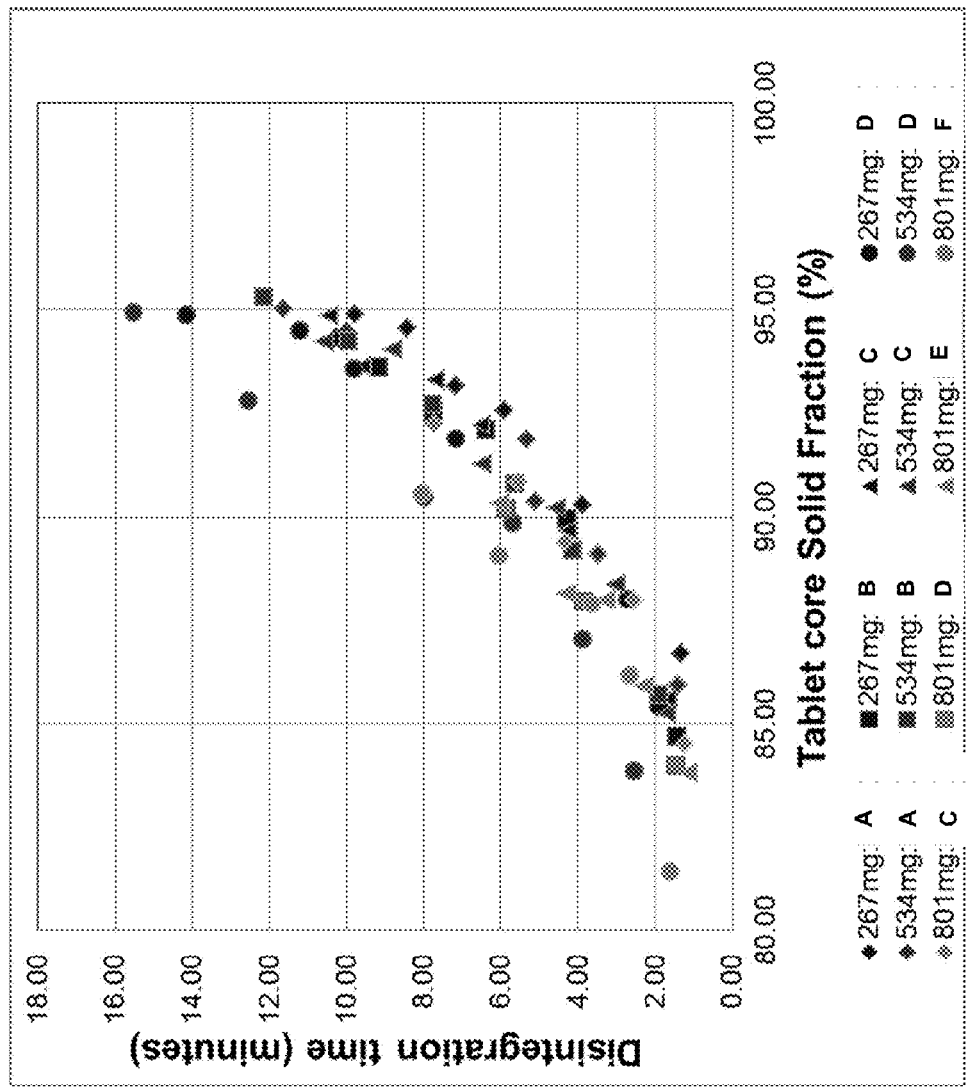
FIG. 5 is a graph illustrating the correlation between disintegration time and tablet core solid fraction for a formulation in accordance with embodiments of the disclosure.
Figure 6:
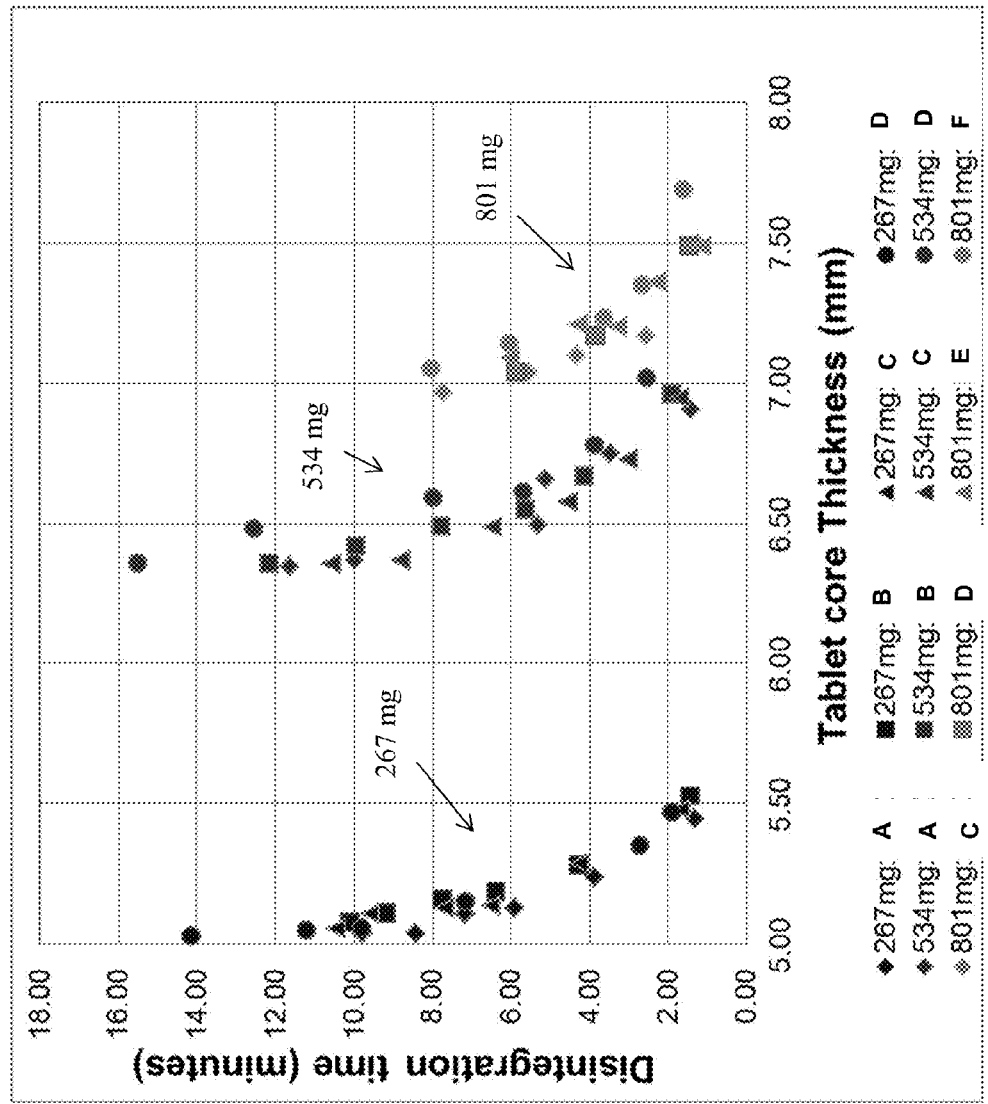
FIG. 6 is a graph illustrating the correlation between disintegration time and tablet core thickness for three dosage strengths of a formulation in accordance with embodiments of the disclosure.

Particle size variations of the drug substance were found to affect the hardness (tensile strength) of a tablet formed from the granulate formulation. It was, however, surprisingly discovered that the solid fraction of the tablets in accordance with the disclosure, and not the tensile strength, influenced the drug release characteristics. Thus, it was determined that tablet thickness, which controls the solid fraction, can be used as a parameter in the tablet compression step instead of tablet hardness to ensure desired drug release characteristics. FIGS. 5 and 6 illustrate the correlation between disintegration time and solid fraction and tablet thickness respectively, for a tablet in accordance with an embodiment of the disclosure.

It has been further discovered that methods of forming pirfenidone granulations and compressing such formulations into tablets can render the properties of the resulting tablets sensitive to particle size variations in the active ingredient and the water content of the formulation produced through various wet granulation methods, such as high shear mixing methods. Surprisingly, processing pirfenidone formulations in accordance with embodiments of the disclosure using a fluid bed granulation process can allow for a formulation process that is significantly less sensitive to moisture content of the granulate and which can accommodate variations in particle size of the active ingredient. As discussed in detail below, methods of forming the granulate formulation in accordance with embodiments of the disclosure can also allow for subsequent formation of tablets that are free of micro-cracks and have sufficient hardness, despite variations in the particle size of the drug substance that may occur, e.g. from supplier to supplier. This can advantageously provide a more robust commercial scale process that can accommodate variations in the particle size without a need to change the tablet manufacturing process or tablet compression conditions.

In accordance with embodiments of the disclosure, a granulate formulation can include granules which include pirfenidone and one or more pharmaceutically acceptable excipients. As used herein, "intragranular components" refers to the ingredients included in the granule. In addition to the granules, the granulate formulation can include one or more excipients added to the granules as extragranular components. As used herein, "extragranular components" refers to ingredients added to the as-formed granules. In various embodiments, the formulation can include pirfenidone and a glidant as intragranular components. It has been found that inclusion of glidant within the granule in an amount of at least about 1% by weight of the formulation advantageously improves the flowability and processability of the granules and the granulate formulations. In various embodiments, the formulations include an effective amount of intragranular glidant to improve powder and/or granule flow characteristics, for example, as measured by a flow function coefficient of about 4 to about 20, about 5 to about 15, or about 10 to about 14. In various embodiments, the pre-granulation powders, granules, and/or granule formulation can have a flow function coefficient of about 4, 5, 6, 7, 8, 9, 10, 11, 12, 13, 14, 15, 16, 17, 18, 19, or 20.

Typically, glidants are utilized only extragranularly to improve the flow of the as-formed granules in the tableting machine, but are not conventionally used or expected to improve flow of a drug substance during granulation. However, it has been advantageously and surprisingly discovered that use of an intragranular glidant in the present formulation with pirfenidone can improve flow of the intragranular components in powder form, improve processing and flow of the granules, and improve flow of the granules with or without the addition of extragranular components during compression, such as in a tableting process. In some embodiments, the formulations of the disclosure can be compressed, for example tableted, without the need for the addition of glidant as an extragranular component.

Figures 2A, 2B:
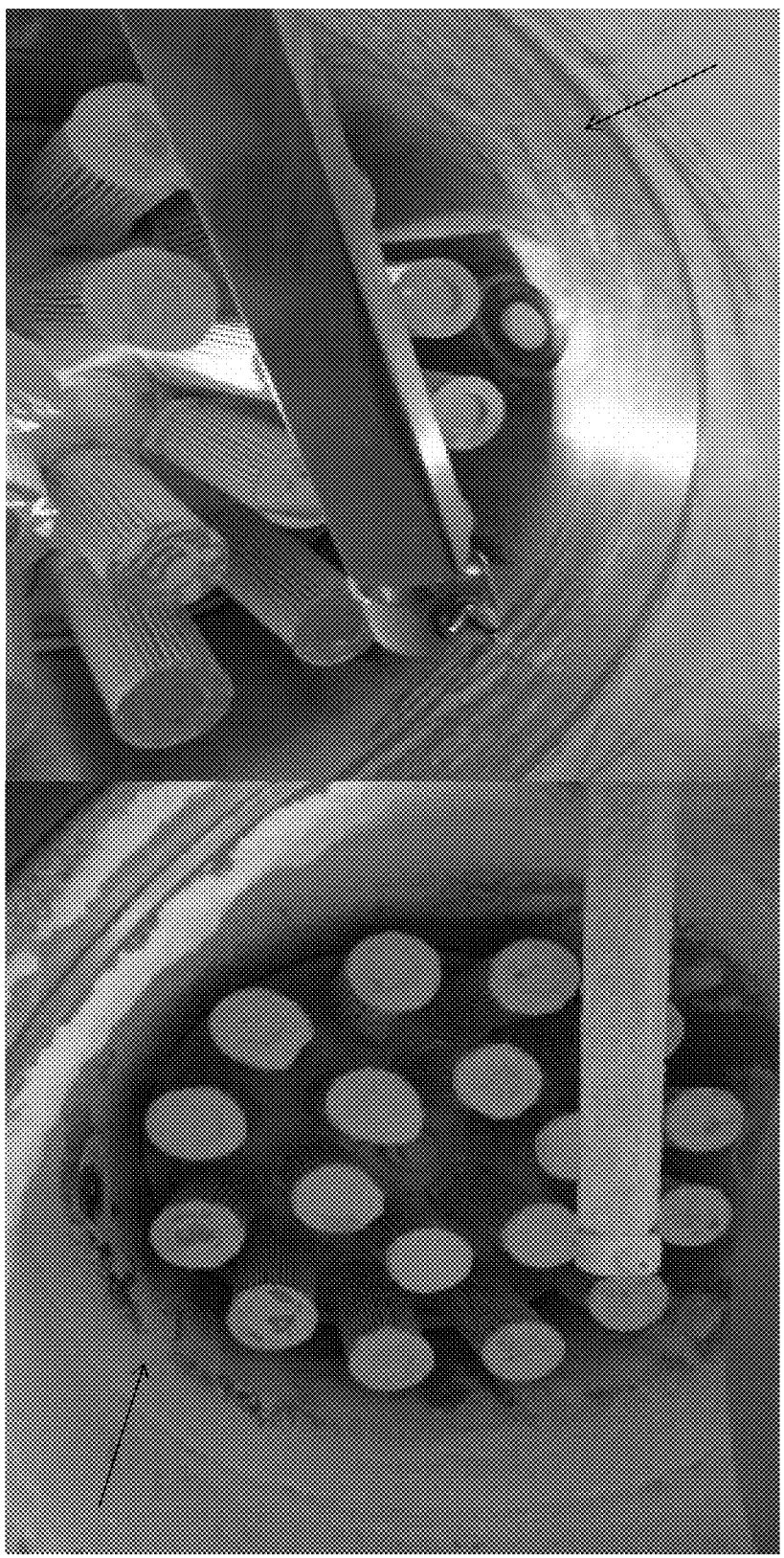
FIG. 2A is a photograph of a granulator bowl after processing a formulation without intragranular glidant.
FIG. 2B is a photograph of a granulator bowl after processing a formulation with intragranular glidant in accordance with an embodiment of the disclosure.

Referring to FIGS. 2A and 2B, formulations with and without glidant were tested. A powder mixture of pirfenidone, filler and glidant was granulated in a granulator bowl using a wet granulation process in which binder was sprayed onto the mixture. It was observed that a reduced amount of granules and residual powder that stuck to the sides of the granulator bowl when the granules contained the intragranular glidant (FIG. 2B). As illustrated in FIG. 2A, without an intragranular glidant, the granules were observed as sticking to the sides of the bowl and a significant amount of residual powder remained stuck to the granulator bowl, which is indicative of the cohesive nature of the formulation.

Additional excipients can be included in some embodiments. Examples of excipients include binders, fillers, disintegrants, lubricants, and further glidants, which can be provided as intragranular and/or extragranular components. For example, in an embodiment, a formulation includes pirfenidone, filler, binder, and a glidant as intragranular components, and a disintegrant, lubricant, and further glidant as extragranular components.

For dosage forms that include coatings, such as film coated tablets, unless specified otherwise, weight by weight percentages (w/w %) of pirfenidone or excipients in the formulation as used herein refer to the weight based on the total weight of the core (e.g., tablet core) and exclude any weight of the exterior coatings.

A formulation can include about 60 wt % to 95 wt % pirfenidone based on the total weight of the formulation. Other suitable amounts include about 70 wt % to about 95 wt %, about 65 wt % to about 90 wt %, about 80 wt % to about 95 wt %. For example, the formulations can include pirfenidone in an amount of about 60, 62, 64, 66, 68, 70, 72, 74, 76, 78, 80, 82, 84, 86, 88, 90, 92 94 and 95 wt % based on the total weight of the formulation. In accordance with embodiments of the disclosure, the unit doses can be provided with a dosage amount of pirfenidone in a range of about 100 mg to about 1100 mg. For example, dosage strengths can include 200 mg, 267 mg, 534 mg, 600 mg, and 801 mg pirfenidone. In alternative embodiments, dosage strengths can include 266 mg, 268 mg, 533 mg, 535 mg, and 800 mg pirfenidone. In an embodiment, the unit dose is a compressed dosage form, for example, tablets.

In accordance with embodiments of the disclosure, formulations of pirfenidone can include one or more excipients selected from the group consisting of binders, disintegrants, glidants, lubricants, and fillers. Excipients conventionally used as binders, fillers, glidants, lubricants, and fillers can be used in the formulations of the disclosure. Example listings of suitable excipients are provided below.

The binder can be selected from the group consisting of hydroxymethyl cellulose, hydroxypropylcellulose, polyvinylpyrrolidone, calcium carbonate, dicalcium phosphate, carbomers, cellulose acetate phthalates, copovidone, hydroxypropyl methyl cellulose, ethylene glycol and vinyl glycol grafted copolymer, isomalt, poloxamer, polyethylene oxide, polymethacrylates, and combinations thereof.

The binder can be included in an amount in a range of about 1 wt % to about 10 wt %, about 2 wt % to about 10 wt %, about 2 wt % to about 5 wt %, about 4 wt % to about 8 wt %, about 3 wt % to about 7 wt, and about 3 wt % to about 5 wt %, based on the total weight of the formulation. Other suitable amounts of binder include about 1, 1.5, 2, 2.5, 3, 3.5, 4, 4.5, 5, 5.5, 6, 6.5, 7, 7.5, 8, 8.5, 9, 9.5, and 10 wt % based on the total weight of the formulation. It has been advantageously found that binder amounts greater than 4 wt % can improve granule flowability and compaction behavior during tableting. Binder amounts ranging from about 3.9 wt % to about 4.8 wt % were found to improve compaction behavior of the granules without significant effect on the dissolution and disintegration characteristics of the formulation. The binder amounts are contemplated for any suitable binder, including polyvinylpyrrolidone.

The disintegrant can be selected from the group consisting of agar-agar, algins, calcium carbonate, carboxymethylcellulose and salts thereof, cellulose, clays, corn starch, croscarmellose sodium, crospovidone, gums, methyl cellulose, polacrilin potassium, sodium alginate, cross-linked polyvinylpyrrolidone, sodium starch glycolate, starch, and combinations thereof. In various embodiments, the disintegrant can be provided both within the granules (intragranularly) and extragranularly in a granulate formulation. Alternatively, the disintegrant can be included only intragranularly or only extragranularly.

The disintegrant can be included in an amount in a range of about 0 wt % to about 10 wt %, 0 wt % to about 10 wt %, about 1 wt % to about 10 wt %, about 2 wt % to about 10 wt %, about 2 wt % to about 5 wt %, about 4 wt % to about 8 wt %, about 3 wt % to about 7 wt, and about 3 wt % to about 5 wt %, based on the total weight of the formulation. Other suitable amounts of disintegrant include about 0, 0.5, 1, 1.5, 2, 2.5, 3, 3.5, 4, 4.5, 5, 5.5, 6, 6.5, 7, 7.5, 8, 8.5, 9, 9.5, and 10 wt %.

The lubricant can be selected from the group consisting of agar, calcium stearate, ethyl oleate, ethyl laureate, glycerin, glyceryl behenate, glyceryl palmitostearate, hydrogenated vegetable oil, magnesium oxide, magnesium stearate, mannitol, poloxamer, glycols, sodium benzoate, sodium lauryl sulfate, sodium stearylstearate, sorbitol, stearic acid, talc, zinc stearate, and combinations thereof.

The lubricant can be included in an amount in a range of about 0.05 wt % to about 2 wt %, about 0.1 wt % to about 1.8 wt %, about 0.5 wt % to about 1.5 wt %, about 1 wt % to about 2 wt %, about 0.05 wt % to about 0.5 wt %, about 0.1 wt % to about 0.8 wt %, or about 0.2 wt % to about 0.6 wt %, based on the total weight of the formulation. Other suitable amounts of lubricant include about 0.05, 0.06, 0.07, 0.08, 0.1, 0.2, 0.3, 0.4, 0.5, 0.6, 0.7, 0.8, 0.9, 1, 1.2, 1.4, 1.6, 1.8, and 2 wt %, based on the total weight of the formulation.

The filler can be selected from the group consisting of calcium carbonate, calcium phosphate, dibasic calcium phosphate, calcium silicate, tribasic calcium sulfate, calcium carboxymethylcellulose and salts thereof, cellulose, dextrin derivatives, dextrin, dextrose, fructose, isomalt, kaolin, lactitol, lactose, magnesium carbonate, magnesium oxide, maltitol, maltodextrins, maltose, mannitol, microcrystalline cellulose, sodium bicarbonate, sodium carbonate, sorbitol, starch, sucrose, sugar, xylitol, and combinations thereof.

The filler can be included in an amount in a range of about 2 wt % to about 30 wt %, about 4 wt % to about 20 wt %, about 10 wt % to about 30 wt %, about 2 wt % to about 10 wt %, and about 6 wt % to about 15 wt % based on the total weight of the formulation. Other suitable amounts include, about 2, 3, 4, 5, 6, 7, 8, 9, 10, 11, 12, 13, 14, 15, 16, 17, 18, 19, 20, 21, 22, 23, 24, 25, 26, 27, 28, 29, and 30 wt % based on the total weight of the formulation. The filler amounts are contemplated for any suitable filler, including microcrystalline cellulose.

The glidant can be selected from the group consisting of silica, fumed silica, silicified cellulose, sodium stearate, magnesium aluminum silicate, pyrogenic silica, hydrated sodium silioaluminate, cellulose, calcium phosphate, sodium lauryl sulfate, pregelatinized starch, talc, and physical or coprocessed combinations thereof. The glidant can be silica, and can be a hydrophilic fumed silica (a.k.a. colloidal silicon dioxide). The glidant can be provided intragranularly and optionally extragranularly. In embodiments in which the glidant is provided both intragranularly and extragranularly, the glidant can be the same or different materials.

The glidant can be included intragranularly in an amount, based on the total weight of the formulation, of at least about 1 wt %, at least about 1.5 wt %, at least about 2 wt %, at least about 2.5 wt %, at least about 3 wt %, at least about 3.5 wt % or at least about 4 wt %. For example, when included intragranularly, the glidant can be in an amount of about 1 wt % to about 5 wt %, about 1.5 wt % to about 4.5 wt %, about 1.5 wt % to about 3.5 wt %, about 2 wt % to about 5 wt %, or about 1 wt % to about 4 wt %. Other suitable amounts of intragranular glidant includes about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, and 5 wt %, based on the total weight of the formulation.

The glidant can be included extragranularly in an amount of about 0 wt % to about 5 wt %, 0 wt % to about 5 wt %, about 0.01 wt % to about 1 wt %, about 0.03 wt % to about 0.8 wt %, about 1 wt % to about 5 wt %, about 0.01 wt % to about 0.05 wt %, about 0.5 wt % to about 3 wt %, about 0.01 wt % to about 0.2 wt %, and about 0.05 wt % to about 1 wt %. Other suitable amounts of extragranular glidant include about 0, 0.01, 0.02, 0.04, 0.06, 0.08, 0.1, 0.2, 0.4, 0.6, 0.8, 1, 1.5, 2, 2.5, 3, 3.5, 4, 4.5, and 5 wt %, based on the total weight of the formulation. The glidant amounts are contemplated for any suitable glidant, including silica.

In one type of embodiment, the extragranular components make up 10 wt % or less of a compressed formulation. The extragranular components can be 10 wt % or less, 10 wt % or less, 8 wt % or less, 7 wt % or less, 6 wt % or less, 5 wt % or less, 4 wt % or less, 3 wt % or less, 2 wt % or less, or in a range of 0.01 wt % to 10 wt %, or 0.01 to 8 wt %, or 0.01 to 6 wt %, or 0.01 to 5 wt %, or 0.01 to 4 wt %, or 0.01 to 3 wt %, or 0.01 to 2 wt %, or 0.01 to 1 wt %, for example.

In various embodiments, the granulate formulation can be compressed into a tablet formulation. It has advantageously been discovered that tablets in accordance with the disclosure have drug release characteristics that correlate to the solid fraction. Solid fraction is a normalized process parameter calculated using the dimension of the tablet core (size of the compression tooling and thickness of the tablet), tablet weight, and true density (in contrast to bulk density) of the final blend. During a standard tablet compression operation, for a given dosage strength, all the other factors that define the solid fraction remain unchanged, with the exception of tablet thickness. Therefore, it has been determined that controlling the thickness of the tablet in a standard tablet compression operation can be used to target a predefined solid fraction during tablet compression, which in turn can be used to target a predefined pirfenidone release characteristic.

In various embodiments, the formulations are immediate release formulations. In such embodiments, it can be desirable to have release of at least 80% of the drug substance in approximately 15 minutes. To achieve such release parameters, the compressed unit doses, for example tablets, can have a solid fraction of at least 80%. In some embodiments, the solid fraction is greater than 80%. For example, the unit dose can have a solid fraction of about 80% to about 95%, about 85% to about 90%, about 90% to about 95%, greater than about 80% to 90%, about 81% to about 95%, and about 82% to about 94%. Other suitable solid fractions include 80%, 81%, 82%, 83%, 84%, 85%, 86%, 87%, 88%, 89%, 90%, 91%, 92%, 93%, 94%, and 95%.

In general, a tablet in accordance with embodiments of the disclosure can have a thickness of about 2 mm to about 10 mm, about 2 mm to about 8 mm, about 3 mm to about 8 mm, and about 5 mm to about 10 mm. While the relationship between disintegration time and solid fraction generally has not varied depending on dosage amount in the embodiments tested, there has been some variation when utilizing tablet thickness as a parameter as shown in FIG. 6. It has been found that drug release of at least about 80% in 15 minutes can be achieved in a compressed dosage form having 801 mg of pirfenidone with a tablet thickness of about 5 mm to about 10 mm; in a compressed dosage form having 534 mg of pirfenidone with a tablet thickness of about 3 mm to about 8 mm; and in a compressed dosage form having 267 mg of pirfenidone with a tablet thickness of about 2 mm to about 8 mm.

Figure 1:
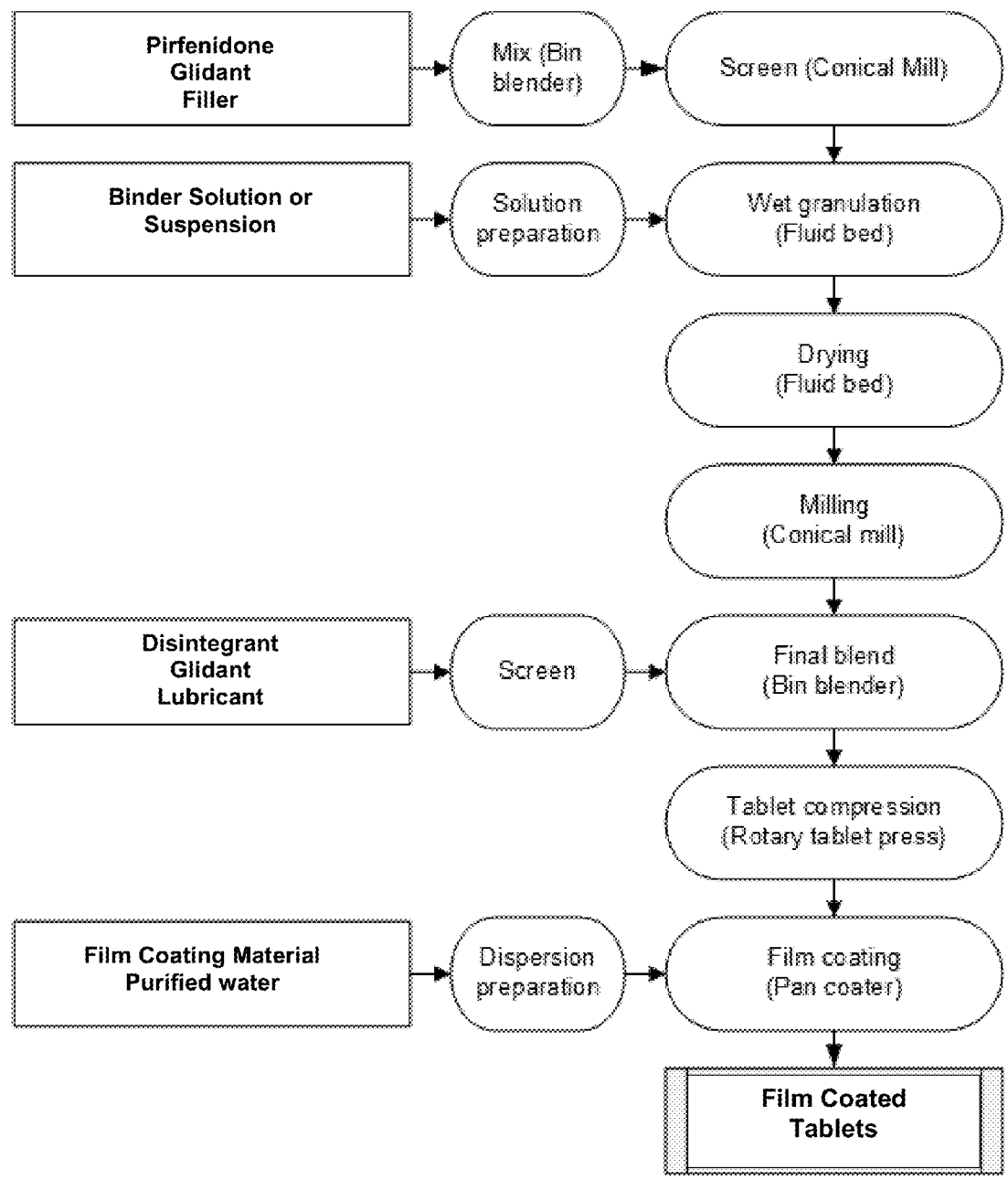
FIG. 1 is a schematic illustration of a process of forming a granulate formulation and film coated tablets in accordance with an embodiment of the disclosure.

Referring to FIG. 1, in an embodiment, a process for forming a granulation in accordance with an embodiment of the disclosure can include mixing pirfenidone with one or more excipients using fluid bed granulation. In various embodiments, the pirfenidone is mixed with a glidant using fluid bed granulation to form an granules. One or more excipients can be added to the granules (extragranularly). It has been advantageously found that use of a fluid bed granulation process can not only improve the processability of the formulation and toleration of pirfenidone particle size variation, but also provide improved tolerance of moisture content in the granulation. For example, when utilizing high shear wet-granulation methods, it was observed that the compressibility of the granules were dependent on a moisture content, requiring a moisture content as measured by loss on drying of 1.5% to 2.0% in order to be processed into tablet cores having suitable physical characteristics (tablet compression to suitable hardness values). However, methods in accordance with the disclosure utilizing fluid bed granulation processing are less sensitive to moisture content, allowing for moisture contents of less than 3%, for example, 0% to 2.9%, thereby accommodating variations (both over- and under-drying) of the granules while allowing for tablets with suitable physical characteristics to be achieved.

Formulations processed with conventional high-shear wet-granulation techniques were also found to be sensitive to changes in pirfenidone particle size distribution from different sources of pirfenidone, resulting in tablets with poor hardness values and oftentimes with microcracks forming in the tablets. By comparison, formulations and methods in accordance with the disclosure were significantly less sensitive to pirfenidone particle size changes and moisture contents, as discussed in detail below. For example, fluid bed granulation can be used. Fluid bed granulation can allow for a multiple-step wet granulation process performed in the same vessel, for example, to do one or more of pre-heat, granulate, and dry the powders.

In an example embodiment, a method of making a formulation in accordance with the disclosure can include mixing pirfenidone and the intragranular excipients to form granules. In various embodiments, the pirfenidone can be mixed with a glidant and a binder or binder solution or suspension to form granules. The granules can further include a filler mixed with the pirfenidone and glidant. In various embodiments, the binder can be added as a solution or suspension. For example, the binder can be sprayed onto the pirfenidone and intragranular excipients. The binder can be provided, for example, as an aqueous solution, aqueous suspension, alcoholic solution, alcoholic suspension, or in an aqueous-alcoholic mixture, which can be a solution or suspension. In some embodiments, the pirfenidone and intragranular excipients can be premixed prior to adding the binder.

The granules can be dried to a target moisture content. For example, drying can be used to remove excess moisture that may have been introduced for example from a binder solution or suspension. Mixing and drying can be completed, for example, using a fluid bed granulator. The granules can then be screened in some embodiments. For example, a 2 mm screen can be used to aid in delumping of the granules. The dried and optionally screened granules can then be mixed with extragranular components. In an embodiment, this can include mixing the granules with a disintegrant and/or a further amount of glidant and/or a lubricant. In an embodiment, the granules are mixed with a disintegrant and further amount of glidant and then the resulting mixture is mixed with a lubricant. In another embodiment, the extragranular components are premixed and added to the granules in a single step.

The method can optionally include heating the pirfenidone and excipients (intragranular) prior to and/or during addition of the solution or suspension of binder. The pre-heating can aid in ensuring the mixture is in a fluidized, mixed state at the time of initiation of the spraying of the binder.

Where multiple extragranular components are added to the granules, the additions can be made simultaneously or serially. For example, in an embodiment, disintegrant, lubricant, and additional glidant are added extragranularly in a single step. In another embodiment, disintegrant and glidant are added extragranularly in a first step and blended and then lubricant is added in a second step with further blending. Any suitable number of addition steps can be utilized.

Optionally, any or all of the drug substance and excipients of the formulation can be premixed and/or screened prior to granulation, for example, prior to charging the components into a granulator bowl. Premixing excipients at the given stages (for example) prior to loading the intragranular components into a mixer or granulator or adding the extragranular excipients to the granules can aid in ensuring good distribution of the components. Screening the excipients and/or premixtures prior to addition can further aid in delump the formulation components prior to loading into the granulator.

In various embodiments, the granulate formulation can be compressed into a compressed dosage form, e.g. a tablet. For example, the formulation can be compressed using a compression pressure of about 50 MPa to about 500 MPa, about 100 MPa to about 400 MPa, about 200 MPa to about 300 MPa, about 100 MPa to about 170 MPa, and about 75 MPa to about 200 MPa. Other suitable compression pressures include about 50, 55, 60, 65, 70 75, 80, 85, 90, 95, 00, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, and 500 MPa.

In some embodiments, a pre-compression force can be applied during the compression process (e.g. tablet making) for a time prior to application of the full main compression force. For example, a pre-compression force of 20-30% of the main compression force can be applied.

Figure 21:
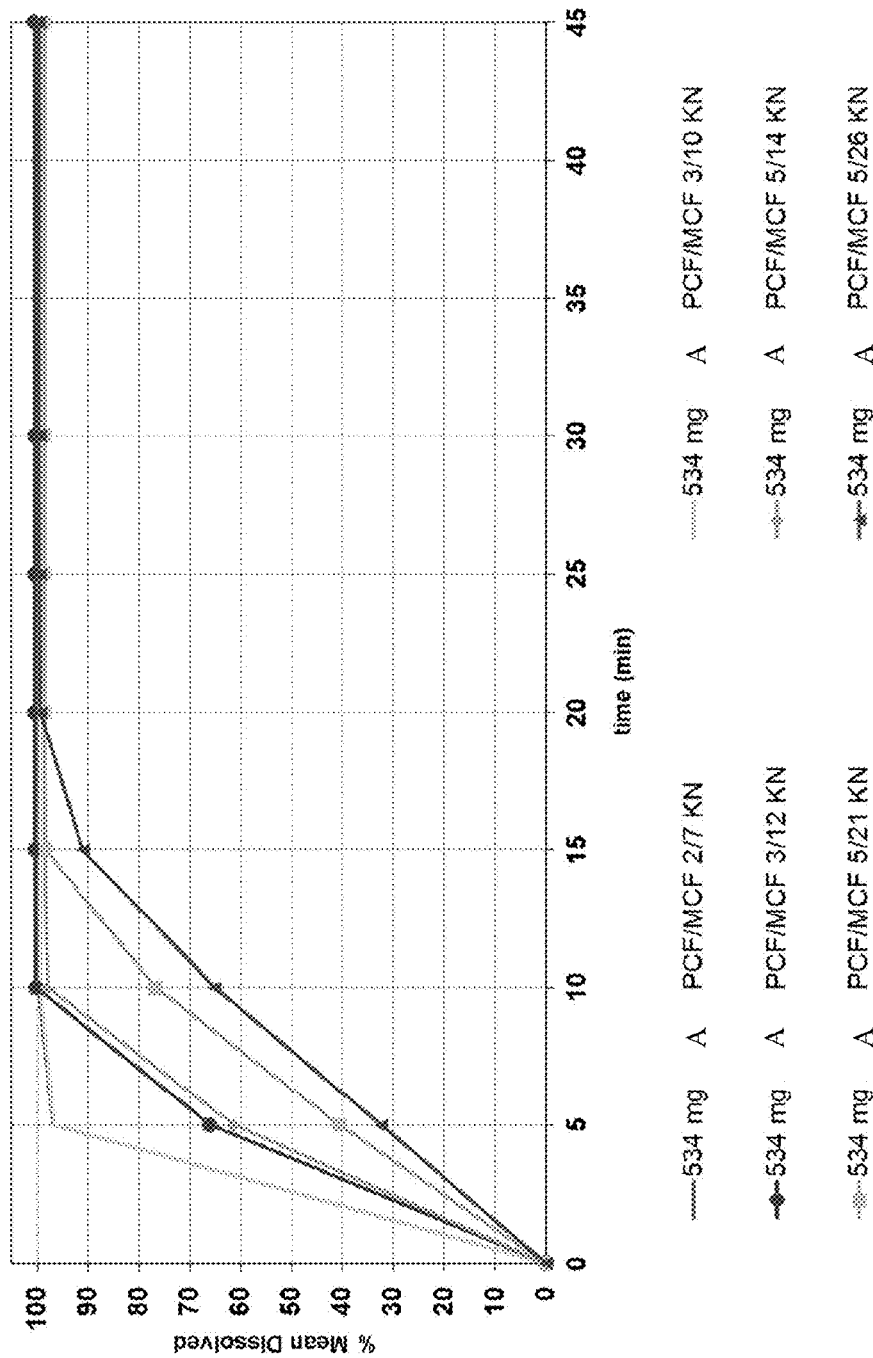
FIG. 21 is a graph of percent drug substance dissolved as a function of time for dissolution of 534 mg pirfenidone tablets in accordance with an embodiment of the disclosure, illustrating the effect of compression force on early stage dissolution.
Figure 22:
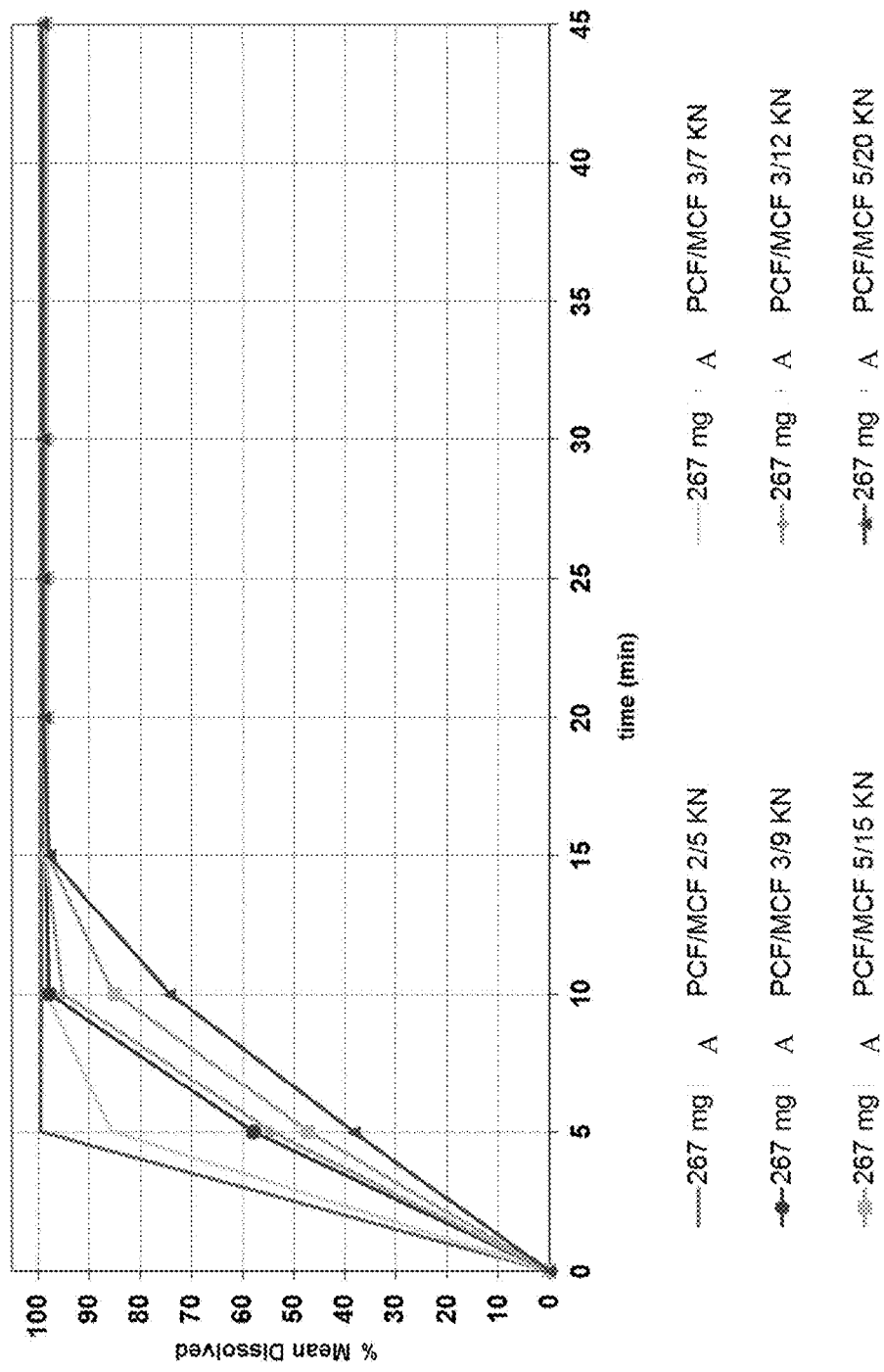
FIG. 22 is a graph of percent drug substance dissolved as a function of time for dissolution of 267 mg pirfenidone tablets in accordance with an embodiment of the disclosure, illustrating the effect of compression force on early stage dissolution.

Compression force can affect the dissolution profile in the early stages of dissolution, generally within the initial 15 minutes. FIGS. 21 and 22 illustrate the changes in the early stage dissolution profile for two dosage strengths (534 mg tablet and 267 mg tablet, respectively) that can result from changing the compression force.

In various embodiments, the compressed dosage form is further coated with a film coating. For example, tablets can be coated with a film coating. In some embodiments, the coating is an immediate release coating. Exemplary coatings including, for example, Opadry II Yellow, Opadry II Pink, and Opadry II Purple. Coatings can be used, for example, to color the dosage form to identify by color, different dosage amounts. Coatings can also include light shielding agents in some embodiments, which can aid in maintaining the photostability of the dosage form. Any coatings and methods of coating compressed dosage forms can be used. Coatings can include one or more of titanium dioxide, iron oxide, talc, polyethylene glycol, and polyvinyl alcohol. The coatings can be applied as a solution using any suitable coating techniques. The coatings can be colored, for example, to differentiate dosage strengths. In various embodiments, the coloring can be provided by a color iron oxide, for example, iron oxide black, iron oxide red, iron oxide yellow, and combinations thereof. In various embodiments, the coatings add 1% to 5% weight to the formulation, for example, a tablet core. Any suitable coating amounts, coat weights, and added weight percentages can be used.

Advantageously, formulations in accordance with embodiments of the disclosure can be compressed into a compressed dosage form without formation of microcracks and with suitable tablet physical properties including tensile strength. The methods and formulations in accordance with the disclosure are capable of tolerating differences in particle size of the drug substance. FIGS. 3 and 4 illustrate the differences in the particle size distribution of drug substance pirfenidone provided by two different suppliers. As shown in detail in the examples, tabletability and compactability of the formulation can be affected by the differences in particle size. Formulations and methods of making such formulations, disclosed herein, for example, using fluid bed granulation, can allow for the formation of compressed dosage forms having suitable physical characteristics despite the variability in particle size of the drug substance. This can allow for a commercial scale process and formulation that can accommodate drug substance regardless of the supplier and any variations in particle size. Further, while it was observed that the particle size variation could result in differences in the tensile strength, it was determined that such differences did not affect the dissolution behavior of the dosage form, which instead was controlled by the solid fraction.

Formulations in accordance with embodiments of the disclosure can comprise any combination of excipients disclosed herein. Formulations in accordance with embodiments of the disclosure can consist of any combination of excipients disclosed herein. Formulations in accordance with embodiments of the disclosure can consist essentially of any combination of excipients disclosed herein. For example, a formulation in accordance with an embodiment of the disclosure can consist of pirfenidone, intragranular glidant, binder, and optionally one or more of a filler, disintegrant, further glidant, and lubricant.

Any of the foregoing embodiments of the granulate formulation can be provided in an oral dosage form. For example, any of the granulate formulations disclosed herein can be provided as a compressed dosage form, e.g. a tablet. Tablets can comprise any combination of excipients disclosed herein. Tablets can consist of any combination of excipients disclosed herein. Tablets can consist essentially of any combination of excipients disclosed herein. For example, tablets in accordance with embodiments of the disclosure can consist of pirfenidone, intragranular glidant, binder, and optionally one or more of a filler, disintegrant, further glidant, and lubricant.

Therapeutic Indications

One embodiment of this disclosure provides methods for treating fibrotic conditions and other cytokine-mediated disorders. These methods comprise administering the formulation of this disclosure to a patient in need thereof. As used herein, a patient "in need of pirfenidone therapy" is a patient who would benefit from administration of pirfenidone. The patient may be suffering from any disease or condition for which pirfenidone therapy may be useful in ameliorating symptoms. Pirfenidone is a known anti-fibrotic agent, so such disorders include fibrotic disorders, such as fibrotic disorders of the lung, kidney, liver, heart, or other organs. Other disorders that would benefit from therapy with pirfenidone include inflammatory disorders or autoimmune disorders. Yet other disorders that would benefit from therapy with pirfenidone include diseases that result in fibrosis, or where accompanying fibrosis is responsible in part for symptoms or complications of the disease, such as infarctions (tissue death), infection, cancer, cirrhosis, and the like. For example, such diseases or conditions include pulmonary fibrosis, idiopathic pulmonary fibrosis, bronchiolitis obliterans, chronic lung transplant rejection, scleroderma, primary focal segmental glomerulosclerosis (FSGC) or membranoproliferative glomerulonephritis (MPGN), idiopathic interstitial pneumonia, interstitial lung disease in systemic sclerosis, a fibrosis condition of the lung, autoimmune lung diseases, benign prostate hypertrophy, coronary or myocardial infarction, atrial fibrillation, cerebral infarction, myocardiac fibrosis, musculoskeletal fibrosis, post-surgical adhesions, liver cirrhosis, renal fibrotic disease, fibrotic vascular disease, scleroderma, Hermansky-Pudlak syndrome, neurofibromatosis, Alzheimer's disease, diabetic retinopathy, and/or skin lesions, lymph node fibrosis associated with HIV, chronic obstructive pulmonary disease (COPD), inflammatory pulmonary fibrosis, rheumatoid arthritis; rheumatoid spondylitis; osteoarthritis; gout, other arthritic conditions; sepsis; septic shock; endotoxic shock; gram-negative sepsis; toxic shock syndrome; myofacial pain syndrome (MPS); Shigellosis; asthma; adult respiratory distress syndrome; inflammatory bowel disease; Crohn's disease; psoriasis; eczema; ulcerative colitis; glomerular nephritis; scleroderma; chronic thyroiditis; Grave's disease; Ormond's disease; autoimmune gastritis; myasthenia gravis; autoimmune hemolytic anemia; autoimmune neutropenia; thrombocytopenia; pancreatic fibrosis; chronic active hepatitis including hepatic fibrosis; acute and chronic renal disease; renal fibrosis; diabetic nephropathy; irritable bowel syndrome; pyresis; restenosis; cerebral malaria; stroke and ischemic injury; neural trauma; Alzheimer's disease; Huntington's disease; Parkinson's disease; acute and chronic pain; allergies, including allergic rhinitis and allergic conjunctivitis; cardiac hypertrophy, chronic heart failure; acute coronary syndrome; cachexia; malaria; leprosy; leishmaniasis; Lyme disease; Reiter's syndrome; acute synoviitis; muscle degeneration, bursitis; tendonitis; tenosynoviitis; herniated, ruptured, or prolapsed intervertebral disk syndrome; osteopetrosis; thrombosis; silicosis; pulmonary sarcosis; bone resorption diseases, such as osteoporosis or multiple myeloma-related bone disorders; cancer, including but not limited to metastatic breast carcinoma, colorectal carcinoma, malignant melanoma, gastric cancer, and non-small cell lung cancer; graft-versus-host reaction; and autoimmune diseases, such as multiple sclerosis, lupus and fibromyalgia; AIDS and other viral diseases such as Herpes Zoster, Herpes Simplex I or II, influenza virus, Severe Acute Respiratory Syndrome (SARS) and cytomegalovirus; and diabetes mellitus. In addition, the methods of the embodiments can be used to treat proliferative disorders (including both benign and malignant hyperplasias), including acute myelogenous leukemia, chronic myelogenous leukemia, Kaposi's sarcoma, metastatic melanoma, multiple myeloma, breast cancer, including metastatic breast carcinoma; colorectal. carcinoma; malignant melanoma; gastric cancer; non-small cell lung cancer (NSCLC); bone metastases, and the like; pain disorders including neuromuscular pain, headache, cancer pain, dental pain, and arthritis pain; angiogenic disorders including solid tumor angiogenesis, ocular neovascularization, and infantile hemangioma; conditions associated with the cyclooxygenase and lipoxygenase signaling pathways, including conditions associated with prostaglandin endoperoxide synthase-2 (including edema, fever, analgesia, and pain); organ hypoxia; thrombin-induced platelet aggregation; protozoal diseases. For example, IPF and scleroderma (or systemic sclerosis) associated interstitial lung disease (SSc-ILD) share overlapping pathologic pathways, most notably the activation and proliferation of fibroblasts, expression of fibrogenic cytokines and growth factors, and progressive interstitial fibrosis (Tzouvelekis et al. 2005; Castro and Jimenez 2010; Collard et al. 2010; Hummers 2010; van den Blink et al. 2010; Richards et al. 2012; Vij and Noth 2012). IPF and SSc-ILD also have biomarkers in common, including CCL 18, SP-A, SP D, KL 6, ICAM-1, VCAM 1, CCL 2, YKL-40, and vWF In any of the methods or uses described herein, the patient may suffer from a disease selected from the group consisting of lung transplantation/chronic rejection, bronchiolitis obliterans, scleroderma, Primary focal segmental glomerulosclerosis (FSGS), membranoproliferative glomerulonephritis (MPGN), Pneumotosis intestinalis, Susac's syndrome, microvascular impairment during chronic catheterization, Hamartomatous disease, blood spinal cord barrier dysfunction following spinal cord injury, corneal perforation, paraneoplastic disease, rhabdomyolysis, pulmonary capillaritis, chronic hyperhomocysteinemia, frontal-subcortical syndrome, Wegener's granulomatosis, acute intestinal microvascular dysfunction, atherosclerotic disease, keratitis, episcleritis/scleritis, cystic fibrosis, polycystic kidney disease, sickle cell disease, dementia, diabetic ulcer, microangiopathy or small vessel disease, hypothyroidism, thrombotic thrombocytopenic purpura, ischemia-reperfusion injury and haemolytic uraemic syndrome.

In any of the methods or uses described herein, the patient may suffer from a disease or disorder selected from one or more of "autoimmune" disorders of the central nervous system (CNS); a dementia that is not Alzheimer's Disease; a patient in need of pirfenidone therapy; a person who would benefit from pirfenidone administration optionally with the proviso that the patient is not suffering from idiopathic pulmonary fibrosis; Absence seizure; acquired immunodeficiency syndrome (AIDS) encephalitis; acute adult respiratory distress syndrome; acute coronary syndrome; acute intestinal microvascular dysfunction; acute myelogenous leukemia; acute or chronic pain; acute or chronic renal disease; acute synoviitis; acute tissue injury; adenovirus infection; adult respiratory distress syndrome; advanced benign prostate hypertrophy (BPH non-cancerous fibrous enlargement of the male prostate gland); AIDS; airway basement membrane collagen deposition; airway hyperresponsiveness; airway inflammation; airway remodeling; akinetic seizure; allergen-induced chronic airway inflammation; allergic and traumatic disorders; allergic conjunctivitis; allergic rhinitis; allergies; allograft vasculopathy; Alzheimer's disease; amylotrophic lateral sclerosis; an acute ischemic event; an atherosclerotic disease; an autoimmune disease; an inflammatory disease; analgesia; angiogenic disorders; arresting the proliferation of and then killing abnormal cells of neoplastic tissue without serious or fatal injury to healthy normal cells and tissues; arteriosclerosis; arthritic conditions; arthritis caused by a microbial infection; arthritis caused by a parasite; arthritis induced by medical products or drugs (including small synthetic molecules as well as purified natural or synthesized peptides or proteins); arthritis pain; ascites; asthma; atherosclerosis; atherosclerosis of the brain vasculature; atherosclerosis of the cardiac vasculature; atherosclerosis of the peripheral vasculature; atherosclerosis of the renal vasculature; atherosclerotic disease; atonic seizure; atrial fibrillation; auto-immune diseases; autoimmune gastritis; autoimmune hemolytic anemia; autoimmune lung diseases; autoimmune neutropenia; bacterial infection; bacterial meningitis; benign and malignant hyperplasias; benign and malignant tumors lymphomas; benign or malignant hyperplasias; benign prostate hypertrophy; bleomycin-induced pulmonary fibrosis; Blood spinal cord barrier dysfunction following spinal cord injury; bone metastases; bone resorption diseases; brain concussion or contusion; brain edema; breast cancer; Bronchial asthma; bronchiolitis obliterans; bursitis; cachexia; cancer; cancer pain; cardiac fibrosis; cardiac hypertrophy; cardiovascular damage; carotid initimal hyperplasia after balloon angioplasty; cerebral infarction; cerebral malaria; Chagas disease; chronic active hepatitis; chronic bronchitis; chronic glomerulonephritis; chronic heart failure; chronic hyperhomocysteinemia; chronic lung transplant rejection; chronic myelogenous leukemia; chronic obstructive pulmonary disease; chronic thyroiditis; classical allergic response; CNS stroke and infarction; colorectal carcinoma; conditions associated with cytokine activity; conditions associated with p38 activity; conditions associated with prostaglandin endoperoxide synthase-2; conditions associated with the cyclooxygenase or lipoxygenase signaling pathways; Congestive heart failure; corneal perforation; coronary or myocardial infarction; coronary restenosis; Crohn's disease; cystic fibrosis; cytomegalovirus; dementia; dental pain; dermal blisters; dermal burns; dermal damage; dermal fibrosis; dermal scars; diabetes mellitus; diabetes mellitus (type II); diabetic nephropathy; diabetic retinopathy; diabetic ulcer; eczema; edema; endotoxemia shock syndrome; endotoxic shock; eosinophilic granuloma; epileptic condition; episcleritis/scleritis; excessive cellular proliferation; excluding acute myocardial infarction; excluding lung transplantation; excluding wound healing; extravasation from blood vessels or blood vessel rupture with hemorrhage into adjacent tissues occlusions (clots or stenosis) of blood vessels; fever; fibromyalgia; fibrosis; fibrosis accompanying tissue injury from cancer; fibrosis accompanying tissue injury from cirrhosis; fibrosis accompanying tissue injury from infarction; fibrosis accompanying tissue injury from infection; fibrosis associated with injured tissues including that of joints; fibrosis associated with injured tissues including that of kidneys; fibrosis associated with injured tissues including that of livers; fibrosis associated with injured tissues including that of lungs; fibrosis associated with injured tissues including that of prostate glands; fibrosis associated with injured tissues including that of skin; fibrosis secondary to asthma; fibrosis secondary to graft-versus-host reaction; fibrosis secondary to lung cancer; fibrosis secondary to viral diseases; fibrotic conditions and other disorders mediated by cytokines; fibrotic disorder; fibrotic disorder of the heart; fibrotic disorder of the kidney; fibrotic disorder of the liver; fibrotic disorder of the lung; fibrotic vascular disease; formation of new fibrotic lesions following tissue injuries; frontal-subcortical syndrome; fungal infections; gastric cancer; general or dermal traumatic or contusion injuries; glomerular nephritis; goblet cell hyperplasia; gout; graft rejection; graft-host disease; graft-host disease following bone marrow transplantation; graft-versus-host reaction; gram-negative sepsis; Grand mal seizure; Grave's disease; haemolytic uraemic syndrome; Hamartomatous disease; headache; heart failure; hemorrhagic shock; Hermansky-Pudlak syndrome; Hermansky-Pudlak Syndrome (HPS) associated pulmonary fibrosis; herniated, ruptured, or prolapsed intervertebral disk syndrome; Herpes Simplex I or II; Herpes simplex infection; Herpes viral infections; Herpes Zoster; HIV viral infection; Huntington's disease; hyperplasia of mucus glands; hypertrophic (post burn injury) scars; hypertrophic scarring (keloids); hypothyroidism; idiopathic interstitial pneumonia; idiopathic or usual interstitial pneumonia; idiopathic pulmonary fibrosis; immunologic phenomena; infantile hemangioma; infantile spasm; inflammatory bowel disease; inflammatory conditions; inflammatory pulmonary fibrosis; influenza virus; influenza virus infection; inhibit post-operative surgical adhesions; inhibit the TGF-β1 induced rise in collagen output in lung and dermal fibroblast cultures; inhibiting effect to the synthesis and release of TNF-α; insect bite; Insulin resistance; insulin resistance in type 2 diabetes; interstitial lung disease in systemic sclerosis; irritable bowel syndrome; ischemia-reperfusion injury; ischemic injury; Kaposi's sarcoma; keratitis; leiomyomas; leishmaniasis; leprosy; Leukemias; liver cirrhosis; liver damage; liver inflammatory disorders; localized edema; lung sarcoidosis; lung transplantation/chronic rejection; lupus; Lyme disease; lymph node fibrosis associated with HIV; Lymphomas; malaria; malignant melanoma; membranoproliferative glomerulonephritis; metastatic breast carcinoma; metastatic melanoma; microangiopathy or small vessel disease; microangiopathy or small vessel disease that is not related to diabetes; microvascular disorder; microvascular impairment during chronic catheterization; microvascular integrity; mucus hypersecretion; multiple myeloma; multiple myeloma-related bone disorders; multiple sclerosis; muscle degeneration; musculoskeletal fibrosis; myasthenia gravis; myocardial fibrosis; myoclonic seizure; myofacial pain syndrome; myofibroblast hypertrophy; neoplastic disease; neural trauma; neurofibromatosis; neurologic injury; neuromuscular pain; non-small cell lung cancer; NULL; ocular neovascularization; organ hypoxia; Ormond's disease; osteoarthritis; osteopetrosis; osteoporosis; other arthritic conditions; other fibrotic disorders; other viral diseases; pain; pain disorders; pancreatic damage; pancreatic fibrosis; paraneoplastic disease; Parkinson's syndrome; Parkinson's disease; Petit mal seizure; Pneumotosis intestinalis; polycystic kidney disease; post-renal dialysis syndrome; post-surgical adhesions; Pre-eclampsia; pressure bruises; prevent formation of new fibrotic lesions following tissue injuries; primary and secondary multiple sclerosis; primary focal segmental glomerulosclerosis; proliferative disorders; protozoal diseases; psoriasis; pulmonary asbestosis; pulmonary capillaritis; Pulmonary fibrosis caused by collagen vascular disease; Pulmonary fibrosis caused by hypersensitivity pneumonitis; Pulmonary fibrosis caused by inhalant exposure; Pulmonary fibrosis caused by sarcoidosis; pulmonary sarcosis pyresis; radiation and drug-induced lung fibrosis; radiation exposure; radiation injury; Reiter's syndrome; relapsing-remitting multiple sclerosis; remodel or remove scar tissue or fibrosis; remove pre-existing fibrotic lesions; renal glomerulosclerosis; reperfusion injury of the brain or myocardium; restenosis; rhabdomyolysis; rheumatoid arthritis; rheumatoid arthritis-associated interstitial lung disease; rheumatoid spondylitis; scleroderma; scleroderma with pulmonary fibrosis; Scrapie; selective autoimmune disorders; selectively arrest scar enlargement; sepsis; septic shock; Severe Acute Respiratory Syndrome; severe pulmonary fibrosis; Shigellosis; sickle cell disease; silicosis; skin disorders including atopic dermatitis urticarial; skin lesions; slow or inhibit the progressive enlargement of fibrotic lesions; solid tumor angiogenesis; spinal multiple sclerosis; stroke; subepithelial fibrosis; sunburn; surgery; surgical sites immediately after keloid resection; Susac's syndrome; systemic lupus erythromatosus; tendonitis; tenosynovitis; thermal burns; thrombin-induced platelet aggregation; thrombocytopenia; thrombosis; thrombotic thrombocytopenic purpura; tissue fibrosis; tissue injuries caused by bacterial or fungal infections; tissue injuries caused by trauma; toxic shock; toxic shock syndrome; trauma-induced arthritis; treating inflammation in respiratory organs or cutis; ulcerative colitis; vascular restenosis; vernal conjunctivitis; vesicant responses (blisters); viral infection; viral or bacterial infections of the CNS; and Wegener's granulomatosis.

According to embodiments, the patient may suffer from an atherosclerotic disease, including but not limited to atherosclerosis of the renal vasculature, cardiac vasculature, brain vasculature and/or peripheral vasculature. As another example, according to any of the embodiments, the patient may suffer from thrombosis, an acute ischemic event, surgery, or an acute tissue injury.

The dosing may be twice or three times daily, with one or more unit doses per intake. According to a particular embodiment, the total daily intake is at least 1200 mg pirfenidone. The total daily intake amount may vary, depending on the patient profile, including among other things the patient's demographic characteristics, physiological and genetic conditions, and disease prognosis. For example, a child or a senior person may be given a lower amount daily than that given to an ordinary adult.

The anti-fibrotic activity of pirfenidone is demonstrated in in vivo animal fibrosis models, as well as in vitro cell culture studies with human or animal lung fibroblasts, dermal fibroblasts, and fibroblast-like cells. Those data indicate that pirfenidone may be an effective agent for preventing and treating post-surgical adhesions, myocardial fibrosis, renal fibrosis, liver cirrhosis, atherosclerosis, and other fibrotic disorders. In vitro cell cultures with human mesenchymal-like cells (including lung fibroblasts, skin fibroblasts, prostate stromal cells, and renal mesangial cells, etc.) have shown pharmacologic inhibition by pirfenidone of excessive cell proliferation induced by cytokine growth factors (TGF-β1, bFGF, PDGF, and EGF). In cell culture media, graded concentrations of pirfenidone were effective at levels which were ten to twenty times lower than those exerting any pharmacologically toxic effects on the cells.

At the site of injury, otherwise normal resident cells (e.g., fibroblasts, pericytes, mesangial cells, astrocytes, microglia, and oligodendrocytes) manufacture and discharge high concentrations of growth factors into adjacent tissue spaces. These resident sources of pathologically high levels of growth factors are directly responsible for the persistently excessive levels of growth factors. They cause excessive and harmful formation of collagen or amyloid matrix as well as damage to adjacent cells, the associated organ dysfunction, and frequently, organ malformation.

TGF-β1 is a potent growth-related peptide whose effects may be observed at femtomolar concentrations. It appears to be ubiquitous, and is a bifunctional regulator of cell proliferation in vitro. It acts either as a mitogen or a growth inhibitor depending on tissue concentration and the state of cell confluence (L. J. Striker et al., Lab. Invest. 64:446-456, 1991). In skin incisions, after attracting macrophages and fibroblasts, TGF-β1 enhances extracellular matrix formation by increasing transcription of genes for collagen and fibronectin, decreasing secretion of proteases, increasing secretion of protease inhibitors, and increasing transcription of cellular receptors for matrix proteins.

The anti-fibrotic activities of pirfenidone have been demonstrated in vivo in laboratory animals with fibrotic lesions, in vitro with human lung fibroblast (WI38) cell cultures, and observed through pilot open trials in patients with severe pulmonary fibrosis, benign prostate hypertrophy, or keloids. Pirfenidone may selectively arrest scar enlargement, and remodels or removes scar tissue or fibrosis. The dysfunction caused by fibrotic lesions may be ameliorated by the reduction or removal of the fibrotic lesion following pirfenidone treatment. Apparently organ and tissue function can be restored, even after the presence of fibrosis for several years. When given immediately after an insult, such as trauma, infection, or allergy, to a tissue, pirfenidone also may prevent formation of excessive scar tissue, or fibrotic lesions, and thus help retain normal function and appearance of the tissue.

Pirfenidone may cause removal of excessive collagenous fibrotic tissue by a phagocytic action of local fibroblasts. This has been observed by examination of histological sections of lung tissue under the light microscope from dogs, mice, rats, and hamsters with pulmonary fibrosis treated with pirfenidone, and also through the electron micrographs of histological sections of lung tissue taken from hamsters with experimentally-induced asbestosis that were treated with pirfenidone. No infiltration of inflammation-inducing neutrophils, PMN cells, monocytes, lymphocytes occurred.

The enhanced proliferation of WI38 fibroblasts upon in vitro exposure to PDGF or bFGF may be blocked by pirfenidone added to cell growth media. Pirfenidone may also inhibit the TGF-β1 induced rise in collagen output in lung and dermal fibroblast cultures.

The human clinical findings after treatment with pirfenidone have been consistent with the anti-fibrotic effects observed in the laboratory animals. Pilot open clinical trials with oral pirfenidone have been undertaken with patients afflicted with pulmonary asbestosis, bleomycin-induced pulmonary fibrosis, idiopathic pulmonary fibrosis, scleroderma with pulmonary fibrosis, and Hermansky-Pudlak Syndrome characterized by pulmonary fibrosis.

The clinical criteria for beneficial response during the first months on pirfenidone included reduction in incidence of coughs, reduction in supplemental oxygen requirements, increased exercise tolerance, reduced dyspnea during exercise, amelioration of cor pulmonale, resumption of normal daily tasks, body weight gain, and survival. During the early months, pulmonary function as gauged by chest x-ray, spirometry, or CO diffusion (DLCO) showed little, if any, change. However, after 4 to 6 months on pirfenidone, inhibition or blocking of further deterioration in lung function was evidenced by pulmonary function tests, vital capacity (VC), in the diffusing capacity of the lung for carbon monoxide (DLCO). These overall observations compare favorably with those described by Van Barneveld et al. (Amer. Rev. Respr. Dis., vol. 135, 48-51, 1987), during the spontaneous recovery by patients from bleomycin-induced pulmonary pneumonitis (early stage fibrosis).

Martinet et al. (NE Jour. Med., vol 317, 202-209, 1987) have described an exaggerated release of PDGF by alveolar macrophages in patients with idiopathic pulmonary fibrosis. The in vitro demonstration of inhibition by pirfenidone of the mitogenesis and enhanced formation of collagen caused by growth factors (bFGF, PDGF, and TGF-β1) may partly explain the beneficial in vivo anti-fibrotic action of pirfenidone.

In an open pilot trial of pirfenidone in older men with clinically advanced benign prostate hypertrophy (BPH, non-cancerous fibrous enlargement of the male prostate gland), the patients experienced functional improvement based on objective criteria. After taking oral pirfenidone the frequent urinary bladder urgency was ameliorated, and nocturia rarely recurred. In another pilot open trial, topical applications of pirfenidone ointment to surgical sites immediately after keloid resection has prevented recurrence of the keloids as observed in two-year follow-ups in the patients. Each of those patients had a prior history of repeated early keloid re-growths after such surgery. Pirfenidone may induce a remodeling of skin fibrotic lesions to reduce or remove keloids, reduce or remove dermal scars, and remove or lessen the contractures of hypertrophic (post burn injury) scars. In a similar condition, pirfenidone also acts to inhibit post-operative surgical adhesions.

Thus, clinical investigations under both controlled protocol designs and open label trials have demonstrated that pirfenidone exerts anti-fibrotic and cytoprotective actions. The observed side effects after oral administration were relatively mild (drowsiness, gastric nausea or photosensitivity rash). No serious adverse reactions have been reported.

Based on the TNF-α inhibitor (cytoprotective) activity of pirfenidone, the formulation of the present disclosure may be administered according to certain embodiments of this disclosure to treat patients suffering from the following disorders:

1) Central Nervous System syndromes: relapsing-remitting multiple sclerosis, primary and secondary multiple sclerosis, spinal multiple sclerosis, cerebral malaria, viral or bacterial infections of the CNS, bacterial meningitis, "autoimmune" disorders of the central nervous system (CNS), CNS stroke and infarction, brain edema, Parkinson's syndrome, Alzheimer's disease, amylotrophic lateral sclerosis (ALS), and brain concussion or contusion;

2) Musculo-skeletal syndromes: rheumatoid arthritis, trauma-induced arthritis, arthritis caused by a microbial infection, or by a parasite, tendonitis, and, arthritis induced by medical products or drugs (including small synthetic molecules as well as purified natural or synthesized peptides or proteins);

3) Pulmonary syndromes: acute adult respiratory distress syndrome, asthma, allergic rhinitis, allergic conjunctivitis, chronic obstructive pulmonary disease (COPD), and lung sarcoidosis;

4) Systemic immunologic, inflammatory or toxic syndromes: endotoxemia shock syndrome, septic shock, graft-host disease, allograft vasculopathy, hemorrhagic shock, reperfusion injury of the brain or myocardium, thermal burns, radiation injury, general or dermal traumatic or contusion injuries, eosinophilic granuloma, diabetic mellitus (type II), or systemic lupus erythromatosus;

5) Gastro-intestinal syndromes: Crohn's disease, ulcerative colitis, and liver inflammatory disorders; and 6) Congestive heart failure. Further, based on the anti-fibrotic activity of pirfenidone, the formulation of the present disclosure may be administered according to other embodiments to treat patients suffering from the following disorders: pulmonary fibrosis, radiation and drug-induced lung fibrosis, hepatic fibrosis, cardiac fibrosis, keloid, post-surgical adhesions, benign prostate hypertrophy in humans, arteriosclerosis, dermal fibrosis, and coronary restenosis.

EXAMPLES

Examples 1 and 2: Formulation

Tablet formulations having good manufacturability were produced having the following components:

TABLE 1

Granulate Formulation

| Component | Function | Example 1 Amount (% w/w) | Example 2 Amount (% w/w) |
|---|---|---|---|
| INTRAGRANULAR COMPONENTS | | | |
| Pirfenidone | Active | 84.23% | 85.3% |
| Microcrystalline Cellulose PH101 | Filler | 6.21% | 6.2% |
| Silica | Glidant | 2.05% | 2.08% |
| Polyvinylpyrrolidone K30 | Binder | 4.64% | 3.83% |
| EXTRAGRANULAR COMPONENTS | | | |
| Croscarmellose sodium | Disintegrant | 1.89% | 1.92% |
| Mg Stearate | Lubricant | 0.50% | 0.19% |
| Silica | Glidant | 0.47% | 0.48% |
| Total (tablet core) | | 100% | 100% |

Example 3: Comparison to Formulation without Glidant

A comparison was made between a pirfenidone formulation with (the formulation of Example 1) and without (comparative example) intragranular glidant. The comparative formulation had the following components:

TABLE 2

Comparative Example

| Component | Function | Amount (%w/w) |
|---|---|---|
| INTRAGRANULAR COMPONENTS | | |
| Pirfenidone | Active | 87.11% |
| Microcrystalline Cellulose PH101 | Filler | 6.33% |
| Silica (Aerosil ® 200) | Glidant | 0% |
| Polyvinylpyrrolidone K30 | Binder | 3.92% |
| EXTRAGRANULAR COMPONENTS | | |
| Croscarmellose sodium | Disintegrant | 1.96% |
| Mg Stearate | Lubricant | 0.20% |
| Silica (Aerosil ® 200) | Glidant | 0.49% |
| Total (tablet core) | | 100% |

Both the formulation of Example 1 and the formulation of the comparative example (Table 2) were processed using fluid bed granulation. As illustrated in FIG. 2A, the comparative example resulted in residual powder remaining stuck to the side walls of the fluid bed granulator. Such sticking of the powder is indicative of the cohesive nature of the intragranular formulation and was found to be an impediment to commercial scale processing of the formulation of the comparative example. By comparison, as shown in FIG. 2B, the formulation of Example 1 did not have a significant amount of residual powder stuck to the side-walls of the fluid bed granulator, resulting in a granulate formulation that was capable of being processed on a commercial scale.

Example 4: Flowability Analysis

Flow function coefficient (FFC) is a measure of powder flow. Values less than about 4 are considered poor and sub-optimal for powder processing. Values between 4-10 are considered acceptable flow values for powder processing. Flow behavior was analyzed for pure pirfenidone (without excipients) and a binary powder mixture of pirfenidone and microcrystalline cellulose mixed with either about 1% by weight silica or about 2% by weight silica, as shown in Table 3 below. The components were mixed in a turbula mixer and the different flow properties of the blends were measured.

TABLE 3

Comparative Test Formulations with and without Silica

| | Pure API | Binary Mixture with ~1 wt. % silica | Binary Mixture with ~2 wt % silica |
|---|---|---|---|
| Pirfenidone | 100% | 92.31% | 91.40% |
| Microcrystalline cellulose PH101 | | 6.70% | 6.64% |
| Silica | | 0.99% | 1.96% |
| Total | 100% | 100% | 100% |

The testing confirmed that pure pirfenidone has poor flow behavior, having a FFC value of 2.3. Adding 1% silica improved the flow behavior slightly, resulting in a mixture with flow properties that were border-line suitable for commercial processing. The 1% silica mixture had an FFC of 3.9. Adding 2% silica resulted in a significant improvement in the flow behavior, resulting in an FCC of 5, which is indicative of good flow.

TABLE 4

Flow Function Coefficient

| | Pure API (pirfenidone only) | Binary Mixture with ~1 wt. % silica | Binary Mixture with ~2 wt % silica |
|---|---|---|---|
| Flow Function Coefficient (Avg.) | 2.3 (poor flow) | 3.0 (borderline flow) | 5.0 (good flow) |

Example 5: Tableting

Tablets were formed from the formulation of Example 1 by applying a compression force of approximately 100 to 170 MPA and utilizing a pre-compression force that was 20-30% of the main compression force. Such compression forces produced tablet cores of solid fraction values between 87% and 93% and tensile strength values greater than 1.6 MPa. The tablets showed good abrasion characteristics (abrasion less 0.5%).

Figure 7:
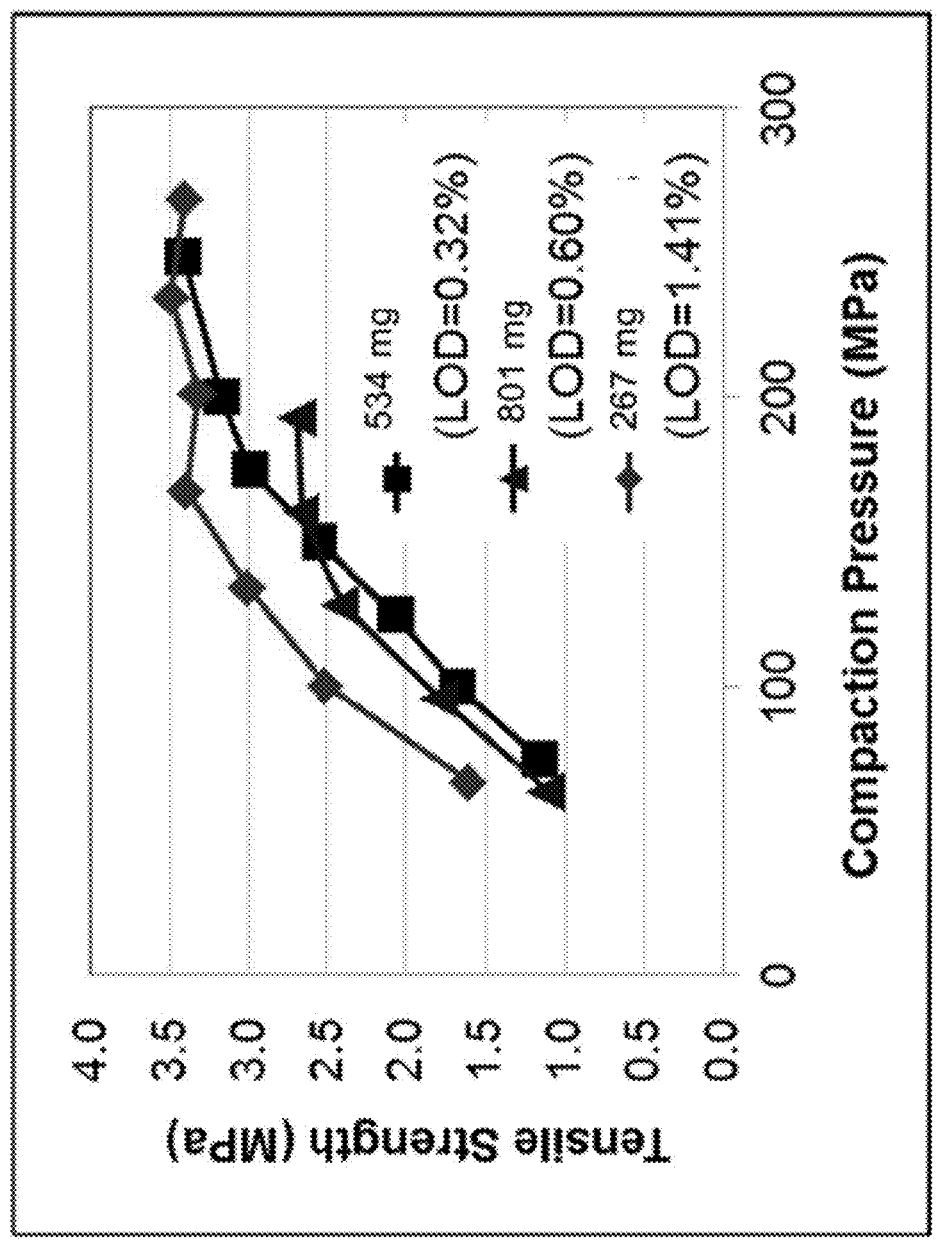
FIG. 7 is a graph illustrating the effect of compression pressure on tensile strength of a compressed dosage form in accordance with an embodiment of the disclosure.
Figure 8:
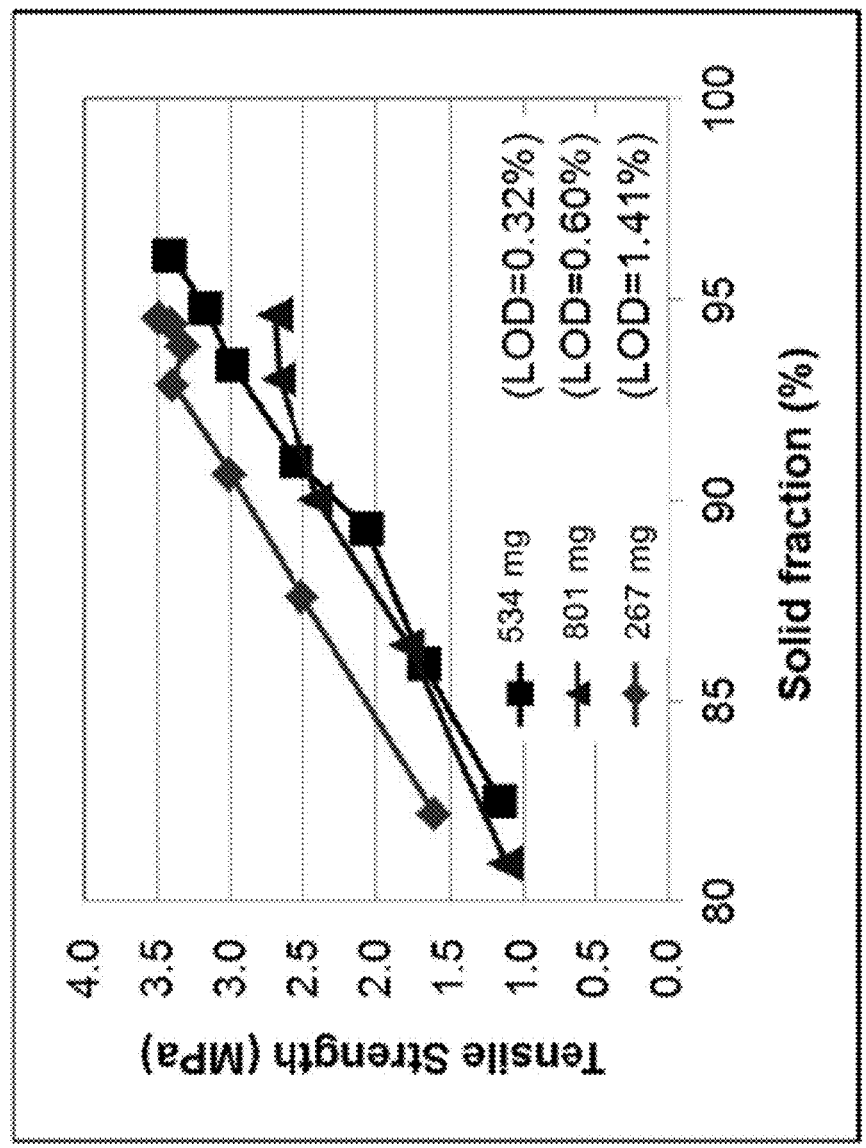
FIG. 8 is a graph illustrating the effect of solid fraction percentage on tensile strength of a compressed dosage form in accordance with an embodiment of the disclosure.

FIGS. 7 and 8 illustrate the tabletability and compactability profiles for tablets having dosage amounts of pirfenidone of 801 mg (triangle symbol), 267 mg (diamond symbol), and 534 mg (square symbol).

Example 6: Disintegration Control

It has been surprisingly discovered that the disintegration of pirfenidone tablets in accordance with embodiments of the disclosure can be controlled by the solid fraction percentage (normalized tablet thickness), independent of the tablet dosage strength. While the particle size of the pirfenidone was found to affect the tablet core hardness, it is the solid fraction and not the tensile strength that was found to influence the drug release characteristics of the tablet cores. This relationship was confirmed over a wide range of pirfenidone particle sizes, from $d_{90}$ of 50-150 µm. Identification of this relationship allowed the tablet core thickness, which controls the solid fraction, to be used as a target parameter in the tablet compression step instead of tablet core hardness.

Solid fraction is a normalized process parameter calculated using the dimensions of the tablet core (size of the compression tooling and thickness of the tablet), tablet weight and true density of the final blend. During a standard tablet compression operation, all the other factors that define the solid fraction remain unchanged, with the exception of tablet thickness. Therefore, controlling the thickness of the tablet can be used to target a predefined solid fraction during tablet compression. Literature studies have shown that tablet solid fraction may have a strong influence on the mechanical strength (or hardness) of a resulting tablet core as well as its disintegration characteristics (Hancock et al., "The relative densities of pharmaceutical powders, blends, dry granulations, and immediate-release tablets," Pharm. Technol. 2003; 27(4):64-80). However, it has been surprisingly discovered that for pirfenidone formulations in accordance with the disclosure, the relationship between the solid fraction (normalized tablet thickness) and the disintegration characteristics of the tablet are independent of the tablet mechanical strength.

For calculation of the solid fraction (Pitt et al., "Compression prediction accuracy from small scale compaction studies to production presses," Powder Tech. 2015; 270 (Part B):490-493), the true density of the final blend was estimated by use of the true density of the pure pirfenidone. The drug load in the pirfenidone film coated tablet composition is very high and the true density of the final blends was expected to be close to that of the pure pirfenidone.

$$SF = \frac{Wt}{\rho true \cdot v}$$

FIG. 5 illustrates the correlation of the disintegration time to the solid fraction percentage, and FIG. 6 illustrates the correlation of disintegration time to tablet core thickness. Identification of this relationship between tablet core thickness and drug release characteristics advantageously provides for control of a drug release properties by readily measureable and controllable parameter—tablet thickness.

Example 7: Bioequivalence

A bioequivalence study was conducted, demonstrating bioequivalence between a film-coated tablet having a formulation in accordance with the disclosure and the commercially available capsule formulation (sold as the ESBRIET® capsule), which is a pirfenidone formulation having no intragranular glidant.

TABLE 5

Formulations Used in Bioequivalence Study

| | ESBRIET® Capsule | Tablet |
|---|---|---|
| | Description | |
| | 267 mg white hard capsule size #1 | 801 mg greyish brown film-coated tablet |
| | Drug Loading | |
| | 82.15% w/w Ingredient | 84.23% w/w$^a$ Ingredient |
| Active pharmaceutical ingredient | Pirfenidone | Pirfenidone |

TABLE 5-continued

Formulations Used in Bioequivalence Study

| | ESBRIET® Capsule | Tablet |
|---|---|---|
| | Description | |
| | 267 mg white hard capsule size #1 | 801 mg greyish brown film-coated tablet |
| | Drug Loading | |
| | 82.15% w/w Ingredient | 84.23% w/w$^a$ Ingredient |
| Filler | Microcrystalline cellulose | Microcrystalline cellulose |
| Glidant (intragranular) | — | Colloidal silicon dioxide |
| Binder | Povidone | Povidone |
| Disintegrant | Croscarmellose sodium | Croscarmellose sodium |
| Lubricant | Magnesium stearate | Magnesium stearate |
| Glidant (extragranular) | — | Colloidal silicon dioxide |
| Film coat | — | Film-coating mixture purple |

The film-coated tablets met the bioequivalence criteria of 90% confidence interval (80.00% to 125.00%) when compared to the capsules in the fasted state, based on $AUC_{0-\infty}$, $AUC_{0-24}$ and $C_{max}$. The film coated tablets met the bioequivalence criteria when compared to the capsules in the fed state with regard to $AUC_{0-\infty}$ and $AUC_{0-24}$, but for $C_{max}$ the upper bound of 90% confidence interval was slightly outside the limit of 125.00%.

Overall, the bioequivalence results indicate that pirfenidone oral exposure is expected to be unaltered by change in formulation from capsule to film-coated tablets.

TABLE 6

Bioequivalence Results Summary in Fasted State

| State of Subjects | Variable | Unit | Ratio Tablets/Capsules | CI 90% Lower | CI 90% Upper |
|---|---|---|---|---|---|
| Fasted | $AUC_{0-\infty}$ | h*ng/mL | 99.61% | 96.64 | 102.68 |
| Fasted | $AUC_{0-24}$ | h*ng/mL | 99.63% | 96.66 | 102.69 |
| Fasted | $C_{max}$ | ng/mL | 101.26% | 94.41 | 108.60 |

Abbreviations:
$AUC_{0-\infty}$ = area under the curve from zero to infinity;
$AUC_{0-24}$ = area under the curve from zero to 24 hours;
CI = confidence interval;
$C_{max}$ = maximal concentration.

TABLE 7

Bioequivalence Results Summary in Fed State

| State of Subjects | Variable | Unit | Ratio Tablets/Capsules | CI 90% Lower | CI 90% Upper |
|---|---|---|---|---|---|
| Fed | $AUC_{0-\infty}$ | h*ng/mL | 103.05% | 99.54 | 106.69 |
| Fed | $AUC_{0-24}$ | h*ng/mL | 103.06% | 99.55 | 106.69 |
| Fed | Cmax | ng/mL | 116.16% | 108.26 | 125.60 |

Abbreviations:
$AUC_{0-\infty}$ = area under the curve from zero to infinity;
$AUC_{0-24}$ = area under the curve from zero to 24 hours;
CI = confidence interval;
$C_{max}$ = maximal concentration.

The bioequivalence of two lower-dose tablets (267 mg and 534 mg) was confirmed by means of a comparative dissolution to the 801 mg tablet tested in the bioequivalence study.

Comparative dissolution profiles of all three strengths are provided in three different media without surfactant, i.e., 0.1N HCl, acetate buffer pH 4.5, phosphate buffer pH 6.8, as well as in the proposed commercial dissolution medium (water). Profiles were recorded with the paddle apparatus (apparatus II) operated at 50 rpm. Twelve samples were measured in 900 mL of the dissolution media described above at 37° C.

Figure 9:
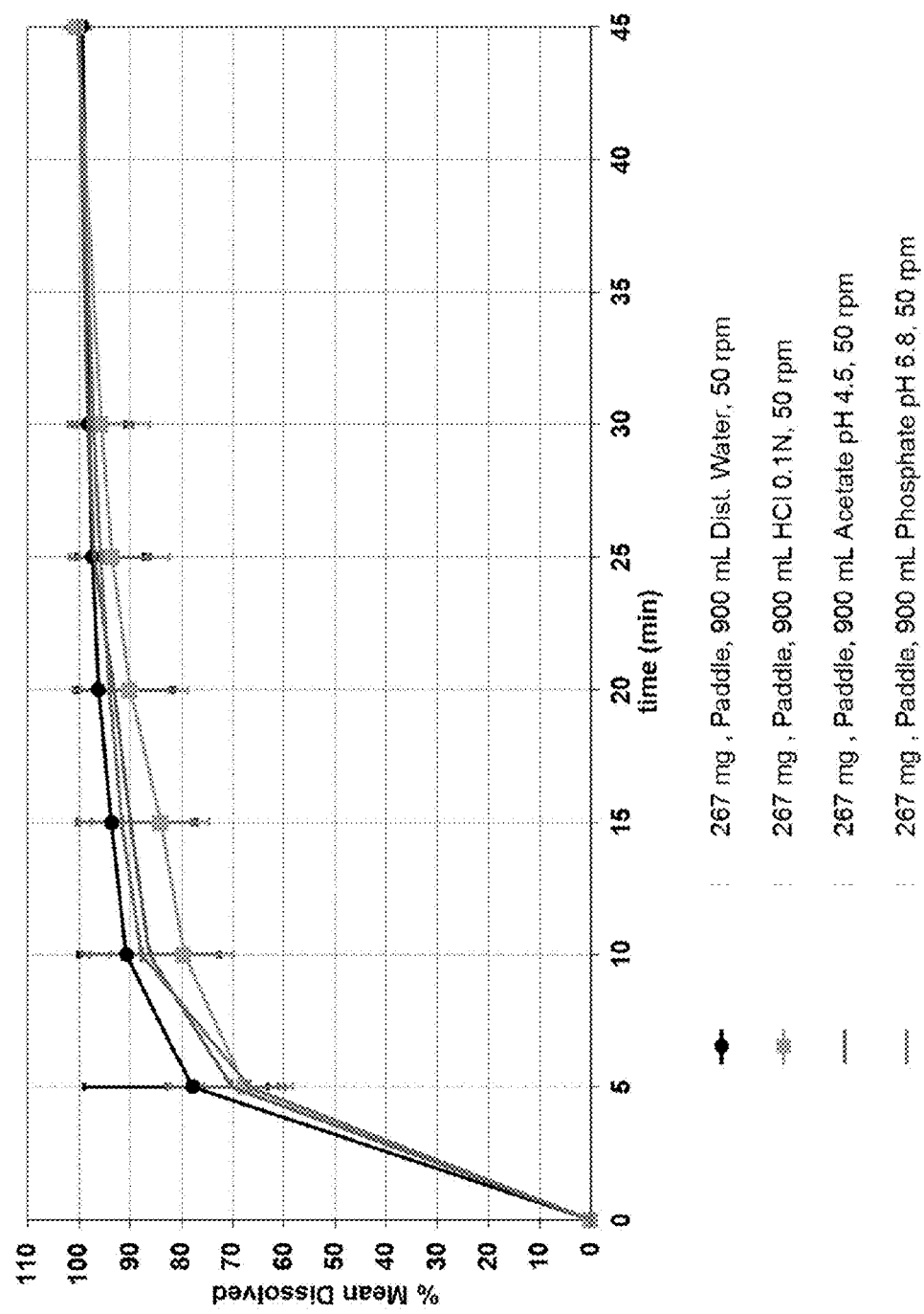
FIG. 9 is a graph of percent drug substance dissolved as a function of time for dissolution of 267 mg commercial pirfenidone capsules in 900 mL HCl 0.1 N, acetate pH 4.5, or phosphate pH 6.8.
Figure 10:
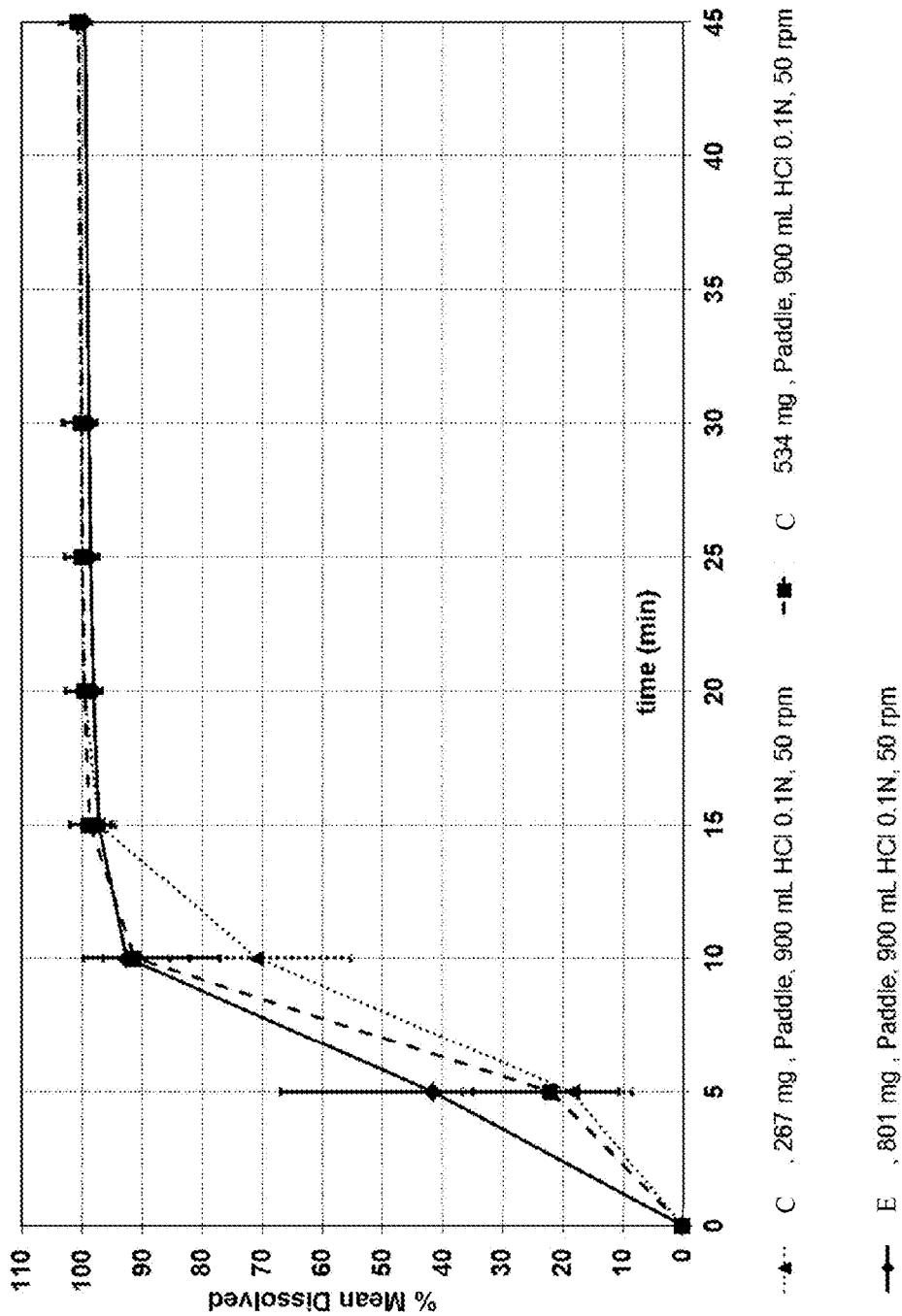
FIG. 10 is a graph of percent drug substance dissolved as a function of time for dissolution of pirfenidone tablets in accordance with embodiments of the disclosure, having dosage strengths of 267 mg, 534 mg, and 801 mg in 900 mL HCl 0.1N.
Figure 11:
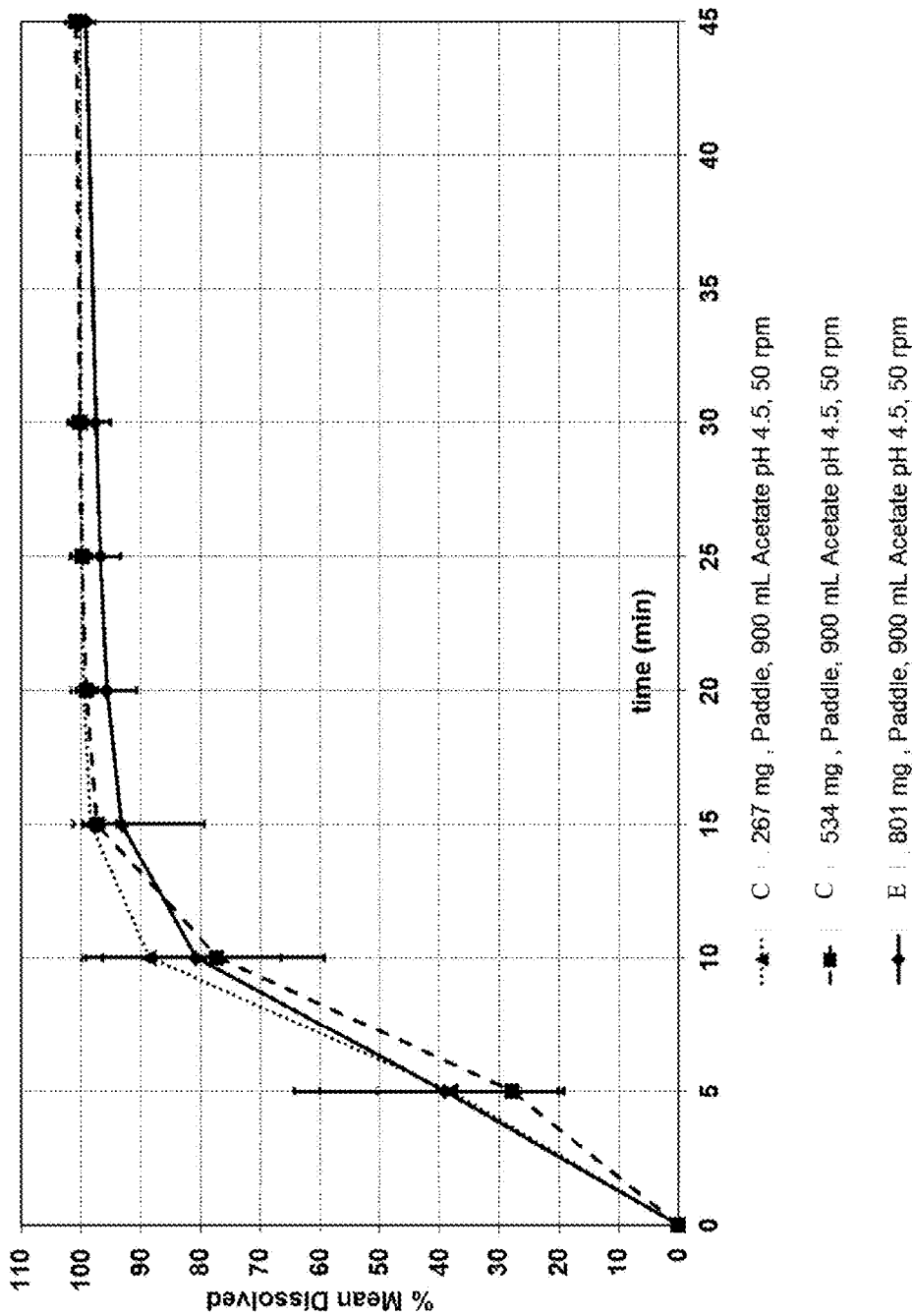
FIG. 11 is a graph of percent drug substance dissolved as a function of time for dissolution of pirfenidone tablets in accordance with embodiments of the disclosure, having dosage strengths of 267 mg, 534 mg, and 801 mg in 900 mL acetate at pH 4.5.
Figure 12:
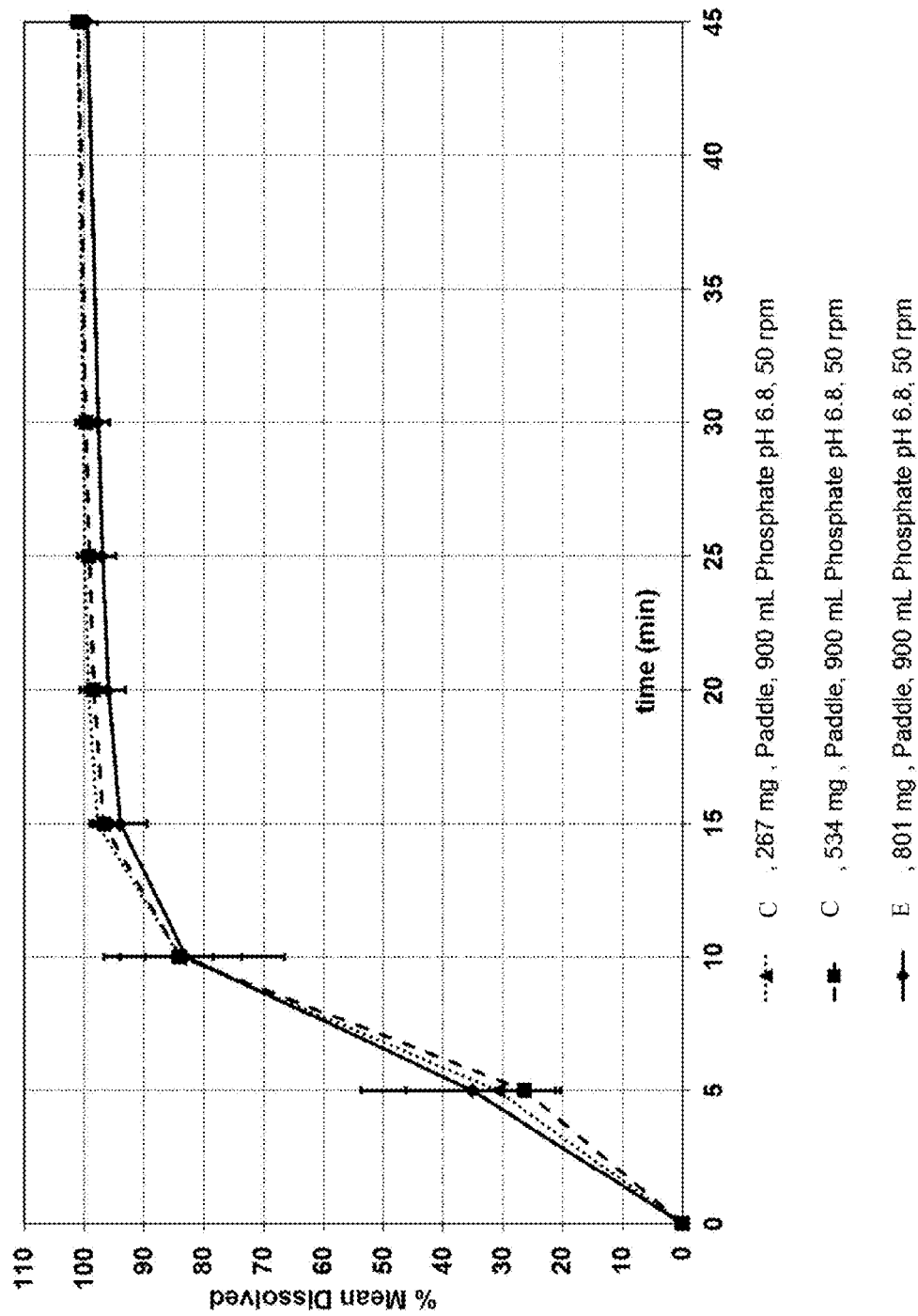
FIG. 12 is a graph of percent drug substance dissolved as a function of time for dissolution of pirfenidone tablets in accordance with embodiments of the disclosure, having dosage strengths of 267 mg, 534 mg, and 801 mg in 900 mL phosphate at pH 6.8.
Figure 13:
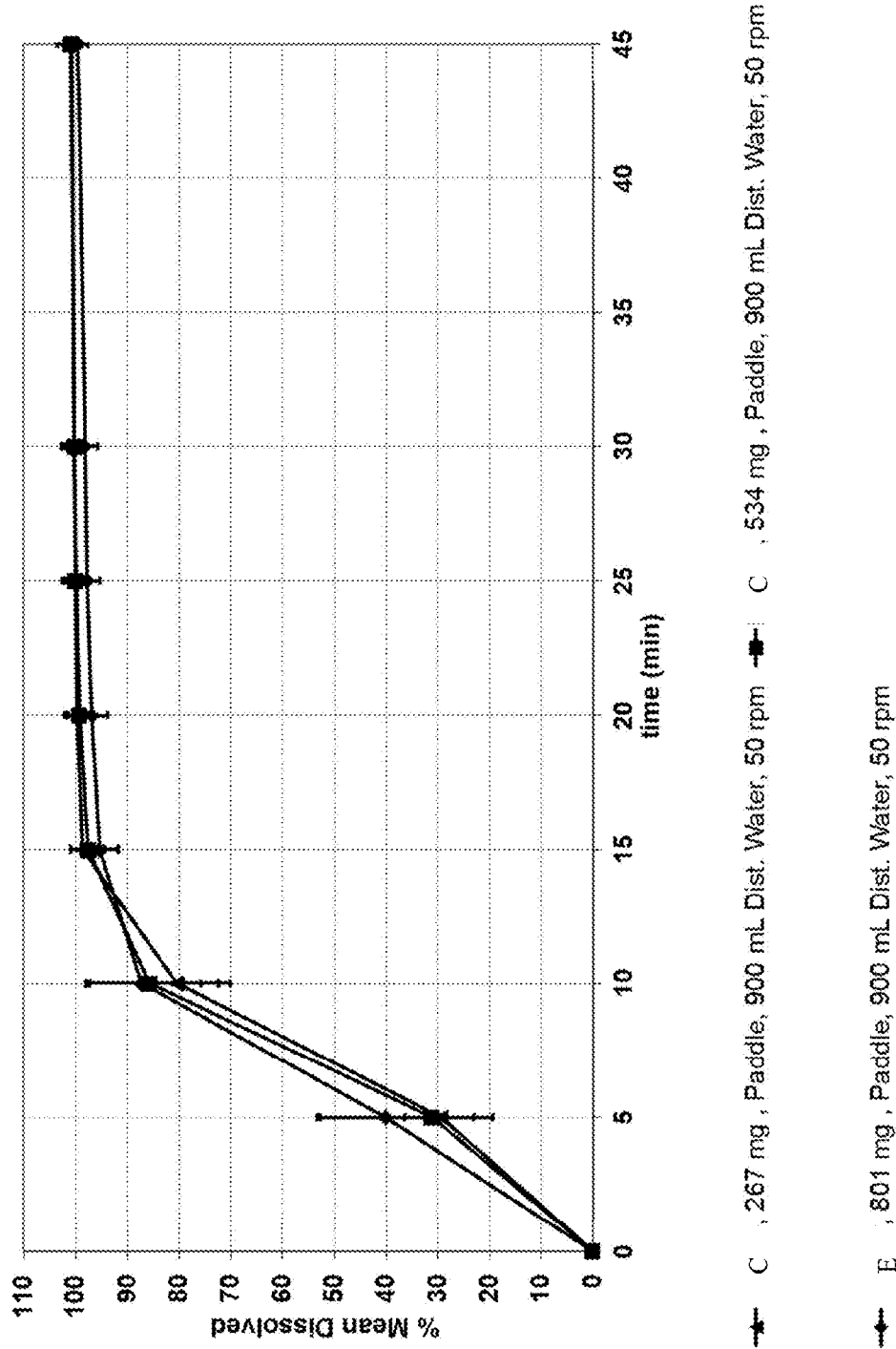
FIG. 13 is a graph of percent drug substance dissolved as a function of time for dissolution of pirfenidone tablets in accordance with embodiments of the disclosure, having dosage strengths of 267 mg, 534 mg, and 801 mg in 900 mL distilled water.

FIG. 9 illustrates the dissolution profile of the hard capsule (267 mg) used in the bioequivalence study.

FIGS. 10-13 illustrate the comparative dissolution profiles for the different tablet strengths tested in four different media: HCl 0.1 N; acetate buffer pH 4.5; phosphate buffer pH 6.8; and water, respectively.

For all strengths tested (801 mg, 534 mg, and 267 mg) in all tested media, the film-coated tablets were found to have an average dissolution of at least 85% at 15 minutes. From this, it was concluded that the lower-dose tablets were also bioequivalent to the capsules.

Example 8: Dissolution Testing

In vitro performance of the film coated tablets in accordance with the disclosure, having a formulation as disclosed in Example 6, was assessed according to the matrix of conditions shown below using Ph. Eur./USP apparatus II, rotating paddles, or Ph. Eur./USP apparatus I, rotating baskets, and 1000 mL of the stated medium at 37° C.

TABLE 8

Dissolution Conditions

| Agitation | Dist. Water | HCl 0.1N | Acetate pH 4.5 | Phosphate pH 6.8 |
|---|---|---|---|---|
| Paddles, 50 rpm | X | X | X | X |
| Paddles, 75 rpm | X | — | — | — |
| Baskets, 75 rpm | X | — | — | — |

Abbreviation: Dist. = distilled.

Figure 14:
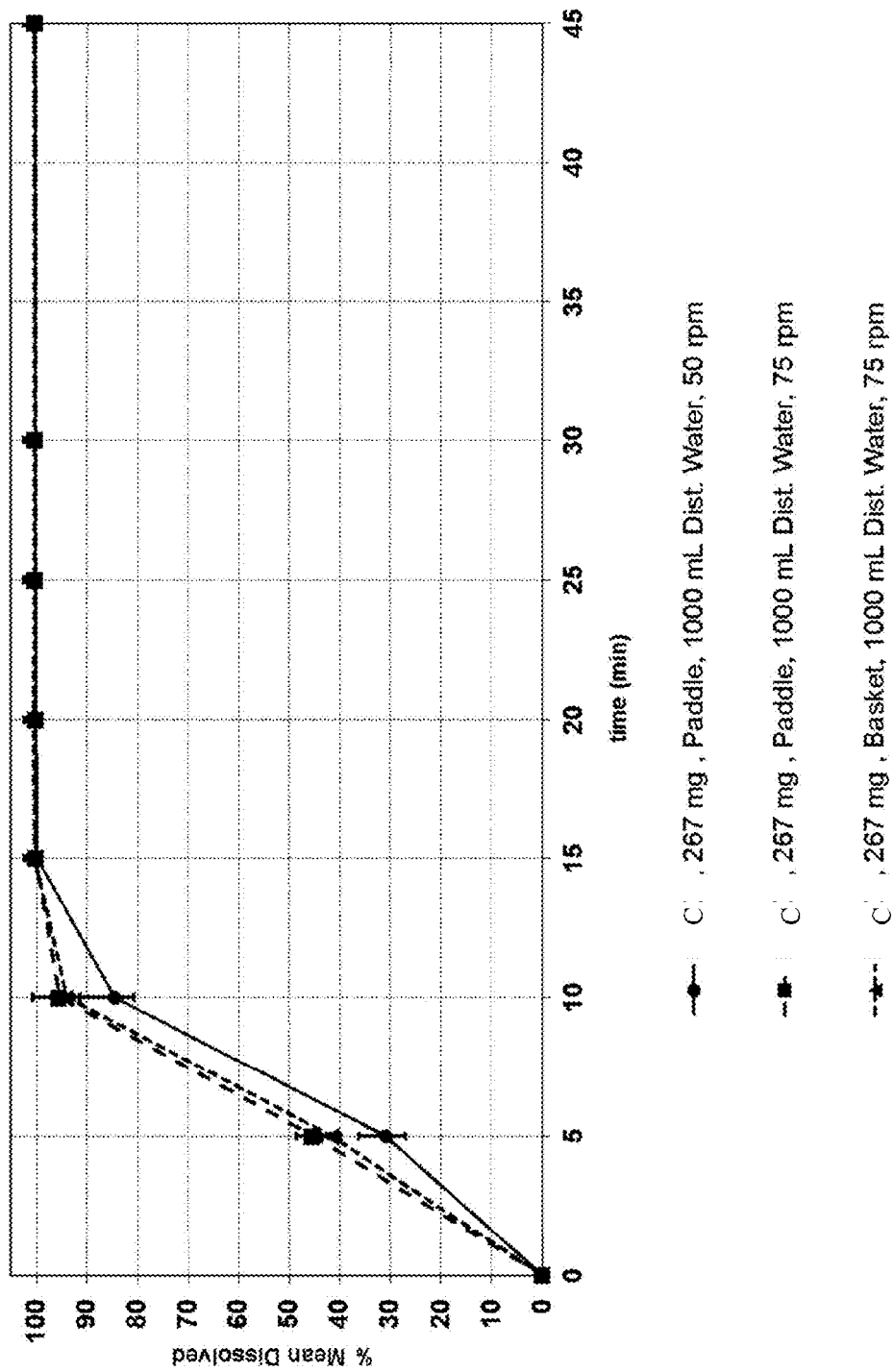
FIG. 14 is a graph of percent drug substance dissolved as a function of time for dissolution of 267 mg pirfenidone tablets in accordance with an embodiment of the disclosure, in 1000 mL distilled water.
Figure 15:
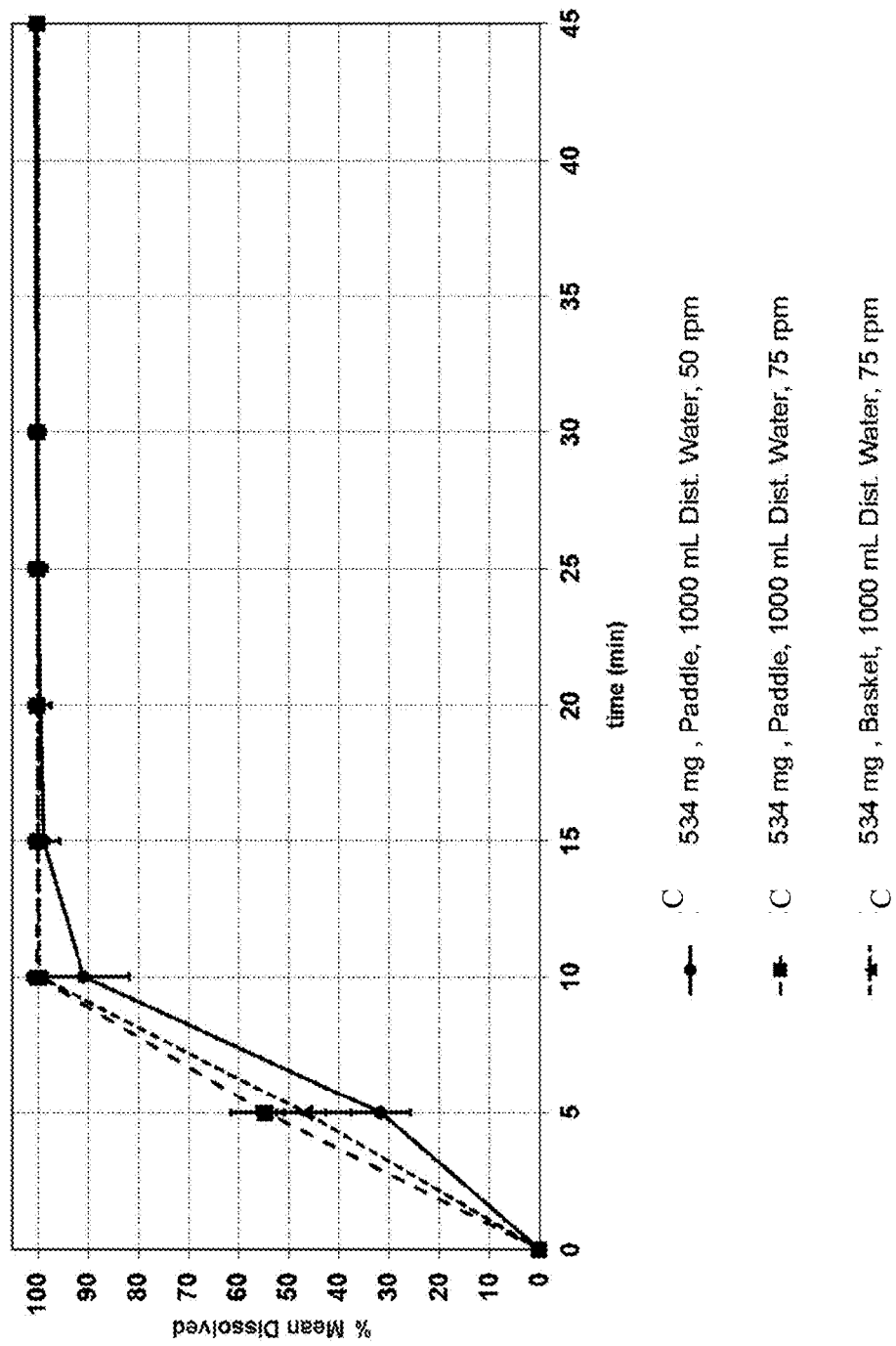
FIG. 15 is a graph of percent drug substance dissolved as a function of time for dissolution of 534 mg pirfenidone tablets in accordance with an embodiment of the disclosure, in 1000 mL distilled water.
Figure 16:
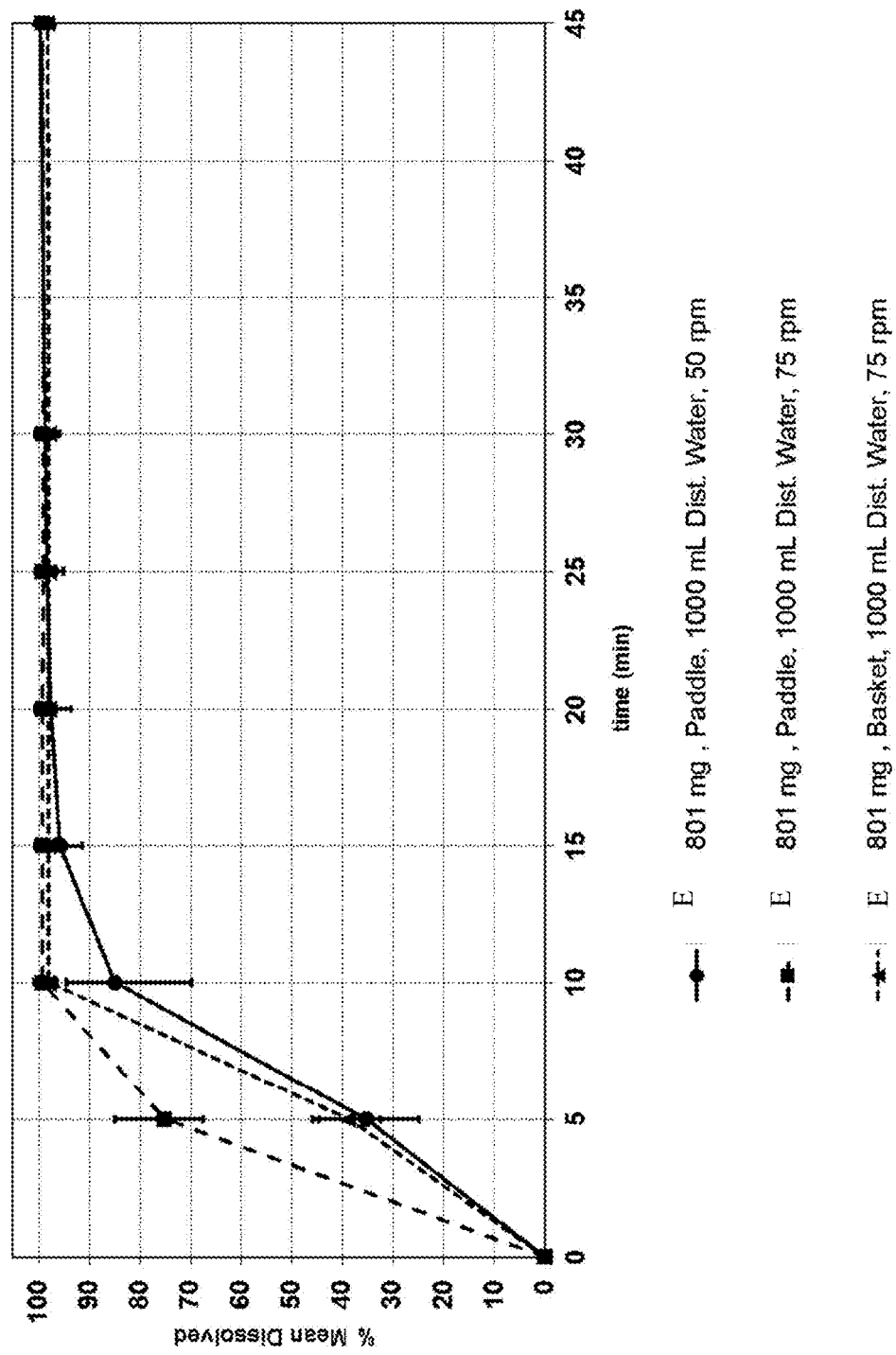
FIG. 16 is a graph of percent drug substance dissolved as a function of time for dissolution of 801 mg pirfenidone tablets in accordance with an embodiment of the disclosure, in 1000 mL distilled water.
Figure 17:
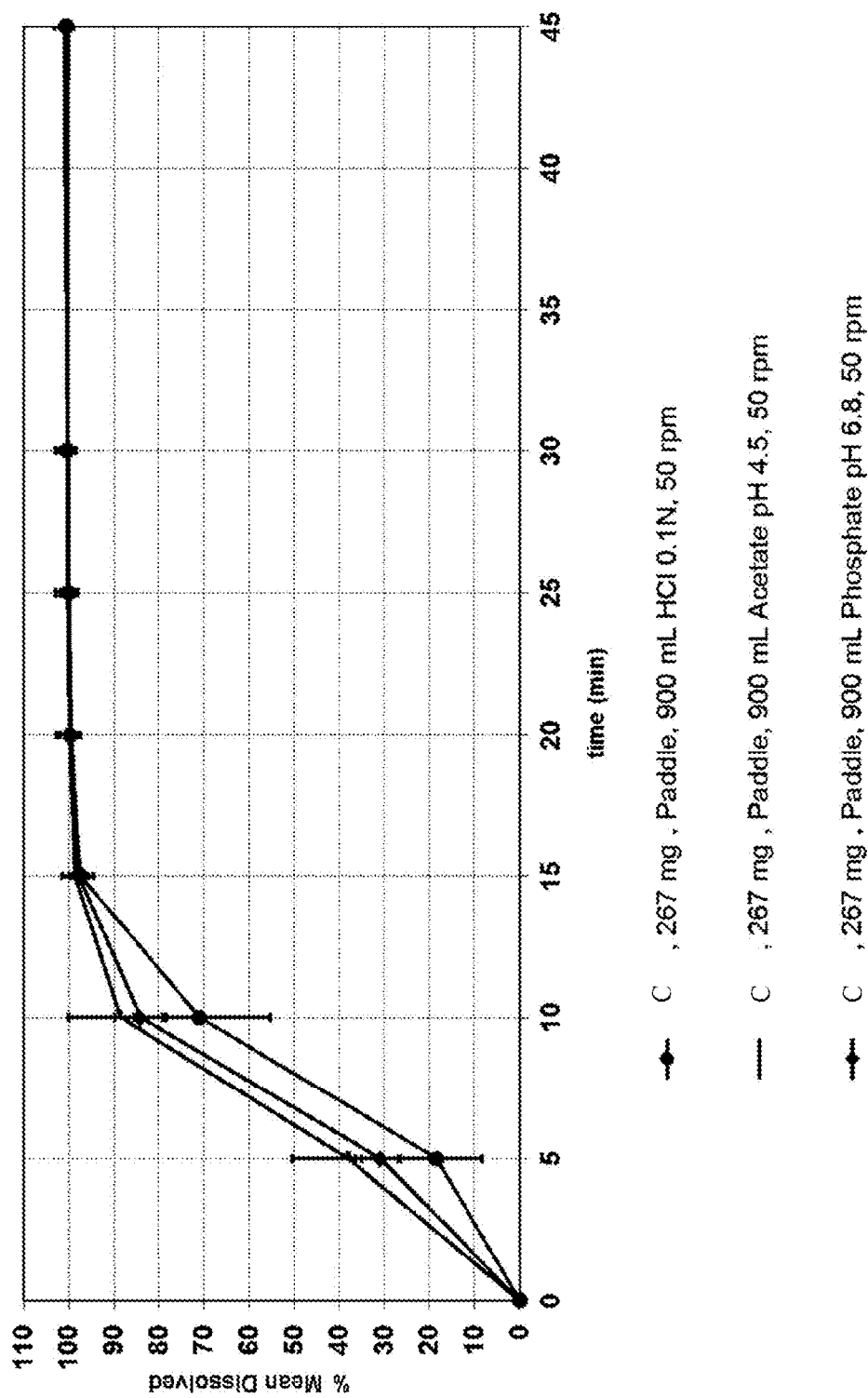
FIG. 17 is a graph of percent drug substance dissolved as a function of time for dissolution of 267 mg pirfenidone tablets in accordance with an embodiment of the disclosure, in 900 mL HCl 0.1 N, acetate pH 4.5, or phosphate pH 6.8.
Figure 18:
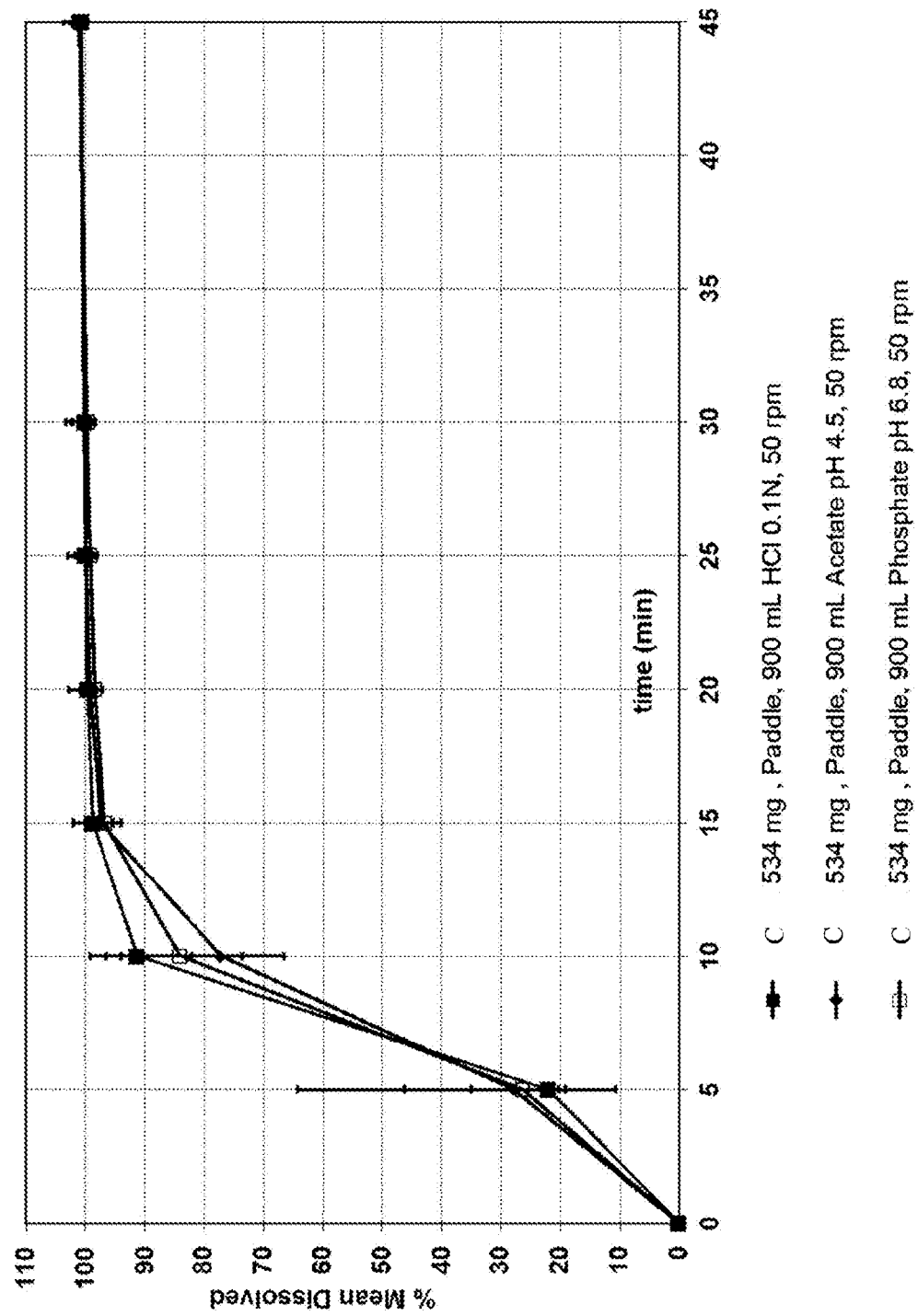
FIG. 18 is a graph of percent drug substance dissolved as a function of time for dissolution of 534 mg pirfenidone tablets in accordance with an embodiment of the disclosure, in 900 mL HCl 0.1 N, acetate pH 4.5, or phosphate pH 6.8.
Figure 19:
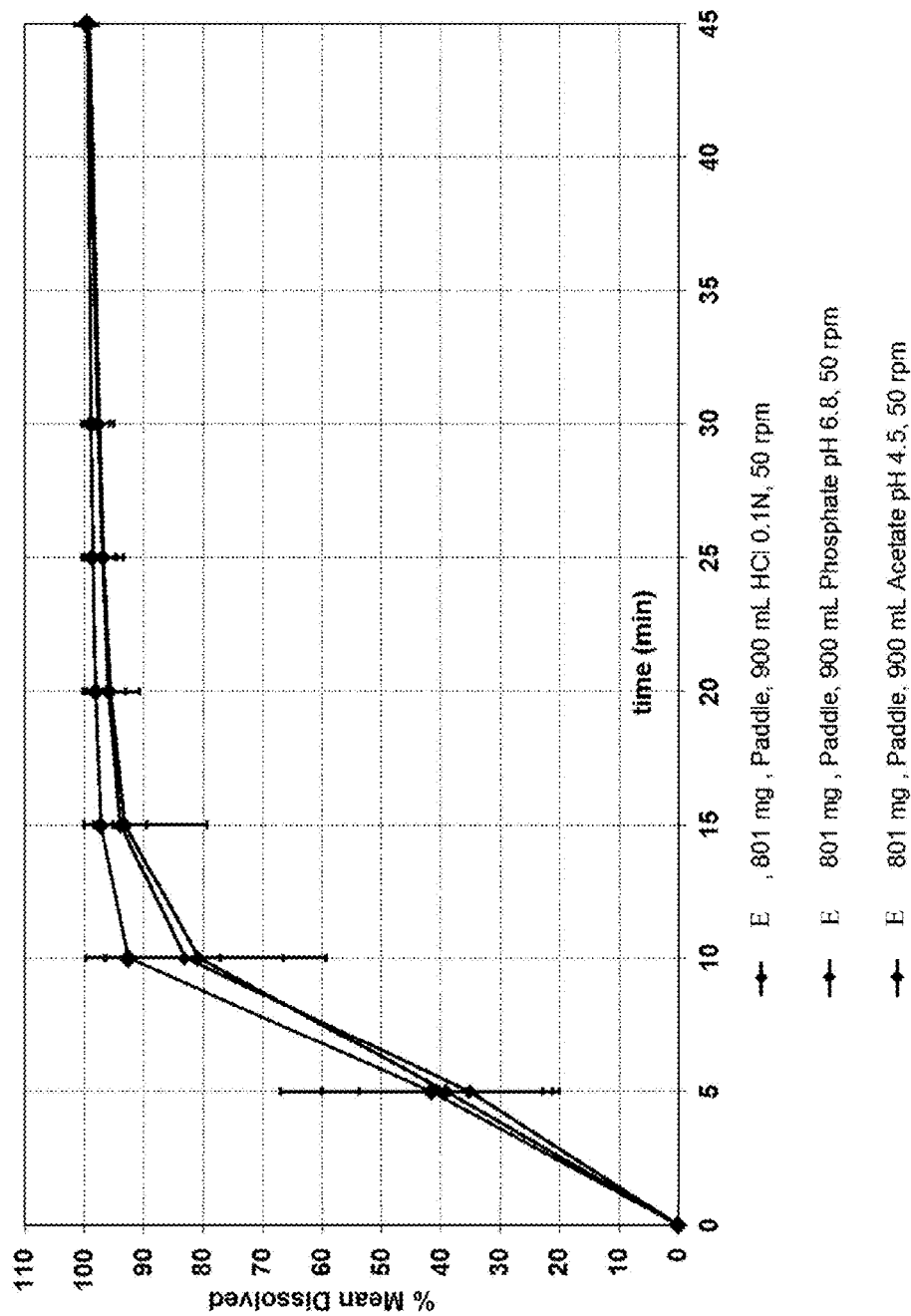
FIG. 19 is a graph of percent drug substance dissolved as a function of time for dissolution of 801 mg pirfenidone tablets in accordance with an embodiment of the disclosure, in 900 mL HCl 0.1 N, acetate pH 4.5, or phosphate pH 6.8.

Aliquots were sampled at 5 minute intervals to ensure generation of data reflecting the ascending part and plateau phase of the profile. Plots of [% mean dissolution] against time were generated for each of the dosage amounts and medium tested. The min/max values are reflected with the error bars. FIGS. 14-16 illustrate the % mean dissolution over time in distilled water for the 267 mg, 534 mg, and 801 mg dosage amounts, respectively. FIGS. 17-19 illustrate the % mean dissolution over time in HCl, acetate, and phosphate for the 267 mg, 534 mg, and 801 mg dosage amounts, respectively.

Dissolution in distilled water with an agitation of 75 rpm using rotating basket (Ph. Eur./USP apparatus I) or 50/75 rpm using paddles (Ph. Eur./USP apparatus II) results in a rapidly dissolving profile (>85% after 15 minutes) and shows an ascending profile between the start of the test up to 15 minutes by reaching a plateau by up to 15-20 minutes for the 801 mg and faster for the other strengths. Under all working conditions a standard deviation around 1% to 3% can be observed after 15 minutes. Dissolution in conventional USP buffers, (HCl 0.1N; 50 mM acetate pH 4.5 and 50 mM phosphate pH 6.8) exhibits similar rapidly dissolving profiles as observed using water with rotating paddles at 50 rpm.

Example 9: Effect of Drug Substance Particle Size on Tablet Properties

Drug substance particle size in the formulations of the disclosure was not found to affect the dissolution of tablets formed form the formulations, where the tablets had the same solid fraction. Formulations with drug substance from two different sources were evaluated. The following tablet provides the particle size distribution information of the sources tested.

TABLE 9

Particle Size Distribution of Two Sources of Pirfenidone

| | DS PSD (µm) | | |
|---|---|---|---|
| Batch ID[a] ... | (D [v, 0.1]) | (D[v, 0.5]) | (D[v, 0.9]) |
| D-801 mg (Source 2) | 16 | 53 | 133 |
| F-801 mg (Source 1) | 11 | 27 | 58 |

Abbreviations:
DS = Drug Substance;
PSD = particle size distribution.
[a]Drug Substance source and batch number is given in bracket.

During dissolution testing, after 10 minutes a plateau was reached and both batches reflected a rapid dissolution over a tested range of process parameters. All tested tablets were 801 mg strength. A main compression force of 10 KN, 20 KN, and 21 KN were tested. Particle size distribution differences resulted in differences in the hardness of the resulting tablets, as illustrated in the table below.

TABLE 10

Tablet Hardness as a Function of Compression Force for Tablets Having Pirfenidone with Different Particle Size Distributions

| Batch ID | Main Compression Force (equiv. Compaction Pressure) | Tablet Hardness (equiv Tensile Strength) | Tablet Thickness (equiv Solid Fraction) |
|---|---|---|---|
| F-801 mg | 10 KN (56 MPa) | 176N (1.3 MPa) | 7.7 mm (81.4%) |
| D-801 mg | 10 KN (59 MPa) | 114N (0.9 MPa) | 7.5 mm (84.0%) |
| F-801 mg | 21 KN (119 MPa) | 265N (2.3 MPa) | 7.1 mm (89.1%) |
| D-801 mg | 20 KN (112 MPa) | 177N (1.6 MPa) | 7.0 mm (90.2%) |

Figure 20:
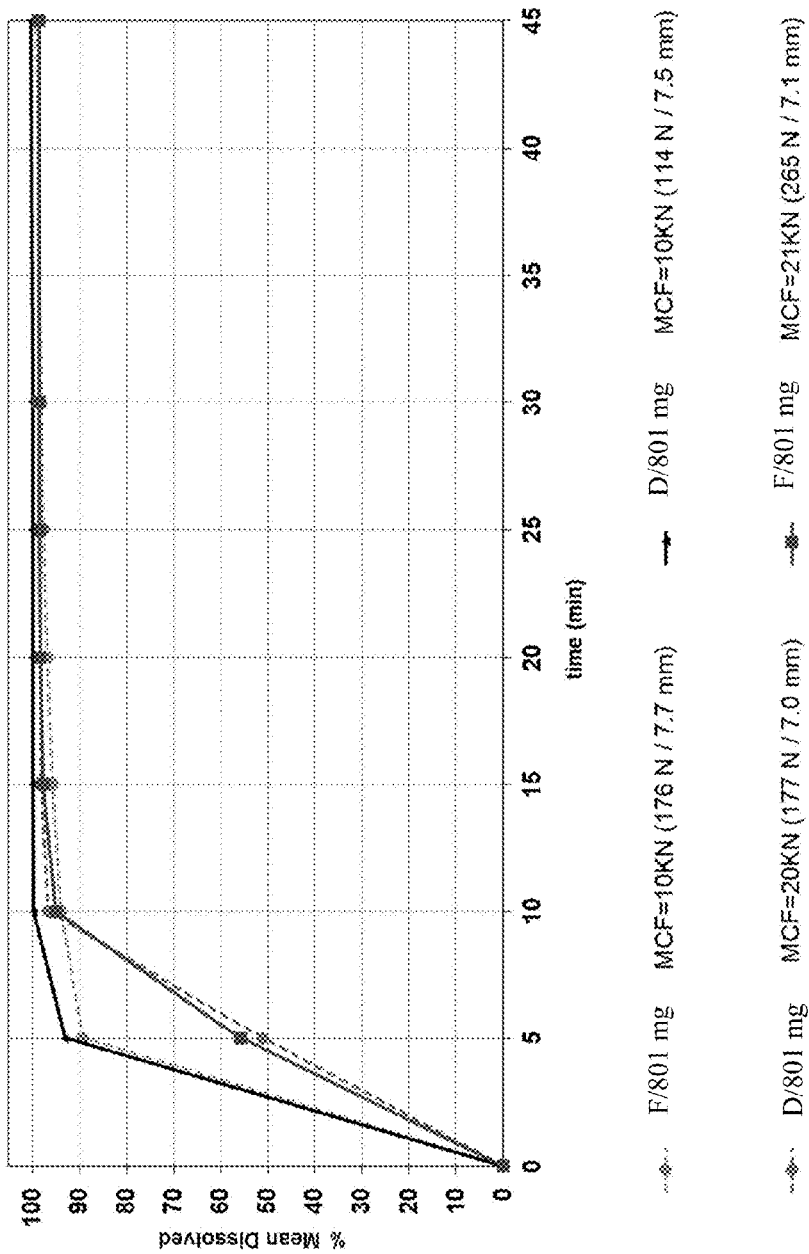
FIG. 20 is a graph of percent drug substance dissolved as a function of time for dissolution of 801 mg pirfenidone tablets in accordance with an embodiment of the disclosure, illustrating the effect of compression pressure and drug substance particle size on dissolution.

As shown in FIG. 20, despite these differences in hardness, the data demonstrate that the dissolution is insensitive to changes in drug substance particle size distribution. Also, tablets compressed to similar thickness values (7.5-7.7 mm versus 7.0-7.1 mm) result in tablets with significant difference in hardness, but that exhibit more comparable dissolution drug release profiles.

Example 10: Effect of Compression Force on Dissolution

Compression force can affect the dissolution profile in the early stages of dissolution, generally after less than 15 minutes. The impact of compression force on the dissolution of three dosage strengths (801 mg, 534 mg, and 267 mg) were studied over a range of 5 KN to 25 KN. The dissolution profile can be affected by the compression force and generally manifested in a change in the shape of the profile during early dissolution stages (between approximately 0-15 minutes). FIGS. 21 and 22 illustrate the changes in the early stage dissolution profile of 534 mg tablets and 267 mg tablets, respectively, that can result from changing the compression force.

Example 11: Fluid-Bed Granulation Process Parameters

Eight batches, each at one of the eight fluid-bed granulation and drying settings of interest, were produced and processed into a final blend. Each final blend was split into two batches, each compressed into tablets to a different hardness setting (120N and 200N).

TABLE 11

Fluid-Bed Granulation Conditions

| Process | Factor Name | Label | Unit | Low | Target | High |
|---|---|---|---|---|---|---|
| Granulation | Inlet air temperature[a] | Inlet air temp | °C. | 50 | 58 | 66 |
|  | Spray rate[a,b,c] | Spray rate | g/min | 375 | 450 | 525 |
|  | Drying time | Drying time | min | 1 | 8 | 15 |
| Tableting | Tablet hardness | Hardness | N | 120 | 170 | 200 |

[a]Same settings of inlet air temperature and inlet air volumes were used in both granulation and drying phases.
[b]The spray rate and inlet air flow volume were combined together into a nominal factor, and varied concurrently. Corresponding air flow volumes: 1600 (low)/1850 (target)/2100 m³/h (high).
[c]Normalized spray rate range equivalent 3.3-4.6 g/min/kg.

Different material attributes of granules, final blend, and tablet cores were measured as responses, with acceptable ranges specified, wherever applicable. Product temperature at the end of drying and loss on drying of the granules were measured as responses to identify if there was a correlation between the two responses. Sieve analysis (to determine the amount of fines), bulk density and flow function coefficients of the final blend were measured as responses which are indicative of the flow behavior of the granules. Where tablets of predefined hardness values were produced, main compression force and tablet thickness were measured as responses. Tablet core attributes of UDU (by mass variation), dissolution at 15 minutes and disintegration time were also studied as responses for the 120N and 200N resulting tablet cores.

All batches were produced using a single drug substance source and compressed into 801 mg strength tablets using the same tooling (20.0×9.3 mm).

Table 12 shows a summary of the effect on the material attributes of the resulting granules.

TABLE 12

Results for Granule Material Attributes

| | Factors | | | | Responses | | | | |
|---|---|---|---|---|---|---|---|---|---|
| Pattern | Inlet air temperature (° C.) | Spray rate-Inlet air volume (g/min-m³/h) | Drying time (min) | Batch # (801 mg Mxxx) | Product temperature at end of drying (° C.) | LOD at end of drying (%) | Final blend (% fines) | Bulk density (g/cm³) | FFC |
| − + − | 50 | 525-2100 | 1 | K | 24.0 | 2.5 | 10.0 | 0.44 | 12.3 |
| + − + | 66 | 375-1600 | 15 | L | 53.1 | 0.6 | 9.4 | 0.40 | 11.6 |
| + + − | 66 | 525-2100 | 1 | M | 32.8 | 1.0 | 27.7 | 0.46 | 9.7 |
| + + + | 66 | 525-2100 | 15 | N | 50.4 | 0.7 | 33.4 | 0.50 | 12.4 |
| − + + | 50 | 525-2100 | 15 | O | 30.9 | 1.1 | 19.1 | 0.45 | 16.4 |
| − − + | 50 | 375-1600 | 15 | P | 32.4 | 1.1 | 16.9 | 0.47 | 13.1 |
| − − − | 50 | 375-1600 | 1 | Q | 23.7 | 2.9 | 13.2 | 0.45 | 14.1 |
| + − − | 66 | 375-1600 | 1 | R | 35.8 | 0.9 | 18.0 | 0.46 | 10.1 |
| 0[a] | 58 | 450-1850 | 8 | I | 37.0 | 0.8 | 22.7 | 0.45 | 13.4 |
| 0[a] | 58 | 450-1850 | 8 | J | 36.7 | 0.8 | 25.2 | 0.45 | 10.6 |

Abbreviations:
DOE = Design of Experiment;
FFC = flow function coefficient;
LOD = loss on drying.
[a]Pseudo-center points.

Table 13 shows a summary of the effect on material attributes of the tablet cores.

TABLE 13

Results for Tablet Core Material Attributes

| | Factors | | | | | Responses | | | | | |
|---|---|---|---|---|---|---|---|---|---|---|---|
| Pattern | Inlet air temp. (° C.) | Spray rate-inlet air flow volume (g/min-m³/h) | Drying time (min) | Hard. (N) | Batch # (801 mg) | Main compression force (KN) (compaction pressure [MPa]) | Mass variation (% RSD) | Thickness (mm) (solid fraction [%]) | Disintegration time (s) | Dissolution at 15 min AVG (%) | Appearance |
| − + − | 50 | 525-2100 | 1 | 200[a] | L | 16.4 (104.8) | 0.64 | 6.66 (97.5) | 337 | 96 | Acceptable |
|  |  |  |  | 120[b] |  | 7.1 (45.4) | 0.56 | 7.07 (90.4) | 81 | 97 | Acceptable |
| + − + | 66 | 375-1600 | 15 | 200[a] | L | 20.3 (129.8) | 0.38 | 6.96 (91.5) | 678 | 94 | Acceptable |
|  |  |  |  | 120[b] |  | 10.4 (66.5) | 0.36 | 7.31 (86.3) | 268 | 99 | Acceptable |
| + + − | 66 | 525-2100 | 1 | 120[b] | M | 8.5 (54.3) | 0.74 | 7.38 (85.0) | 69 | 97 | Acceptable |
|  |  |  |  | 200[a] |  | 15.8 (101.0) | 0.67 | 6.99 (91.0) | 230 | 96 | Acceptable |
| + + + | 66 | 525-2100 | 15 | 200[a] | N | 19.2 (122.7) | 0.56 | 6.94 (92.0) | 463 | 97 | Acceptable |
|  |  |  |  | 120[b] |  | 9.7 (62.0) | 0.65 | 7.44 (84.7) | 140 | 98 | Acceptable |
| − + + | 50 | 525-2100 | 15 | 120[b] | O | 10.3 (65.8) | 0.45 | 7.32 (86.7) | 87 | 97 | Acceptable |
|  |  |  |  | 200[a] |  | 19.7 (125.9) | 0.51 | 6.94 (92.5) | 362 | 98 | Acceptable |

TABLE 13-continued

Results for Tablet Core Material Attributes

| | Factors | | | | | Responses | | | | | |
|---|---|---|---|---|---|---|---|---|---|---|---|
| Pattern | Inlet air temp. (° C.) | Spray rate-inlet air flow volume (g/min-m³/h) | Drying time (min) | Hard. (N) | Batch # (801 mg) | Main compression force (KN) (compaction pressure [MPa]) | Mass variation (% RSD) | Thickness (mm) (solid fraction [%]) | Disintegration time (s) | Dissolution at 15 min AVG (%) | Appearance |
| - - + | 50 | 375-1600 | 15 | 120[b] | P | 9.4 (60.1) | 0.66 | 7.36 (85.7) | 88 | 97 | Acceptable |
| | | | | 200[a] | | 19.3 (123.4) | 0.75 | 6.93 (92.7) | 446 | 98 | Acceptable |
| - - - | 50 | 375-1600 | 1 | 200[a] | Q | 13.8 (88.2) | 0.56 | 6.88 (93.7) | 308 | 95 | Acceptable |
| | | | | 120[b] | | 6.6 (42.2) | 0.57 | 7.19 (87.8) | 84 | 96 | Acceptable |
| + - - | 66 | 375-1600 | 1 | 200[a] | R | 17.9 (114.4) | 0.69 | 6.93 (92.3) | 364 | 98 | Acceptable |
| | | | | 120[b] | | 9.5 (60.7) | 0.80 | 7.37 (85.0) | 108 | 98 | Acceptable |
| 0[c] | 58 | 450-1850 | 8 | 200[a] | I | 20.2 (129.1) | 0.60 | 6.92 (92.4) | 282 | 98 | Acceptable |
| 0[c] | 58 | 450-1850 | 8 | 120[b] | J | 10.6 (67.8) | 0.75 | 7.32 (85.9) | 59 | 97 | Acceptable |

Abbreviations:
AVG = average;
DOE = Design of Experiment;
Hard. = tablet core hardness; RSD = relative standard deviation;
temp. = temperature.
[a]Approximate tensile strength = 1.7-1.8 MPa.
[b]Approximate tensile strength = 0.9-1.0 MPa.
[c]Pseudo-center points.

The foregoing describes and exemplifies the invention but is not intended to limit the invention defined by the claims which follow. All of the formulations and methods disclosed and claimed herein can be made and executed without undue experimentation in light of the present disclosure. While the materials and methods of this invention have been described in terms of specific embodiments, it will be apparent to those of skill in the art that variations may be applied to the materials and/or methods and in the steps or in the sequence of steps of the methods described herein without departing from the concept, spirit and scope of the invention.

All patents, publications and references cited herein are hereby fully incorporated by reference. In case of conflict between the present disclosure and incorporated patents, publications and references, the present disclosure should control.

Throughout this application, the term "about" is used to indicate that a value includes the standard deviation of error for the device or method being employed to determine the value.

What is claimed is:

1. A granulate formulation of 5-methyl-1-phenyl-2-(1H)-pyridone, comprising:
    granules comprising 5-methyl-1-phenyl-2-(1H)-pyridone and a glidant; and
    one or more extragranular excipients comprising an extragranular glidant.

2. The formulation of claim 1, wherein the granules comprise the glidant in an amount of at least about 1% by weight based on total weight of the formulation.

3. The formulation of claim 1, wherein the granulate formulation comprises the extragranular glidant in an amount of about 0.1% to about 5% by weight, based on the total weight of the formulation.

4. The formulation of claim 1, wherein one or both of the glidant and the extragranular glidant is selected from the group consisting of silica, silicified cellulose, sodium stearate, magnesium aluminum silicate, pyrogenic silica, hydrated sodium silioaluminate, cellulose, calcium phosphate, sodium lauryl sulfate, pregelatinized starch, talc, and physical or coprocessed combinations thereof.

5. The formulation of claim 1, wherein the 5-methyl-1-phenyl-2-(1H)-pyridone is present in an amount of about 60% to about 95% by weight, based on the total weight of the formulation.

6. The formulation of claim 1, wherein the granulate formulation comprises one or more pharmaceutically acceptable excipients selected from a disintegrant, a binder, a filler, and a lubricant.

7. The formulation of claim 6, wherein, when present:
    the disintegrant is selected from the group consisting of agar-agar, algins, calcium carbonate, carboxymethylcellulose and salts thereof, cellulose, clays, corn starch, croscarmellose sodium, crospovidone, gums, methyl cellulose, polacrilin potassium, sodium alginate, cross-linked polyvinylpyrrolidone, sodium starch glycolate, starch, and combinations thereof;
    the binder is selected from the group consisting of hydroxymethylcellulose, hydroxypropylcellulose, polyvinylpyrrolidone, calcium carbonate, dicalcium phosphate, carbomers, cellulose acetate phthalates, copovidone, hydroxypropyl methyl cellulose, ethylene glycol and vinyl glycol grafted copolymer, isomalt, poloxamer, polyethylene oxide, polymethacrylates, and combinations thereof;
    the filler is selected from the group consisting of calcium carbonate, calcium phosphate, dibasic calcium phosphate, calcium silicate, tribasic calcium sulfate, calcium carboxymethylcellulose and salts thereof, cellulose, dextrin derivatives, dextrin, dextrose, fructose, isomalt, kaolin, lactitol, lactose, magnesium carbonate, magnesium oxide, maltitol, maltodextrins, maltose, mannitol, microcrystalline cellulose, sodium bicarbonate, sodium carbonate, sorbitol, starch, sucrose, sugar, xylitol, and combinations thereof; and
    the lubricant is selected from the group consisting of agar, calcium stearate, ethyl oleate, ethyl laureate, glycerin, glyceryl behenate, glyceryl palmitostearate, hydrogenated vegetable oil, magnesium oxide, magnesium stearate, mannitol, poloxamer, glycols, sodium benzoate, sodium lauryl sulfate, sodium stearate, sorbitol, stearic acid, talc, zinc stearate, and combinations thereof.

8. The formulation of claim 6, wherein, when present:
the binder is present in an amount of about 1% to about 10% by weight based on the total weight of the formulation;
the disintegrant is present in an amount of 0% to about 10% by weight based on the total weight of the formulation;
the filler is present in an amount of about 2% to about 30% by weight based on the total weight of the formulation; and
the lubricant is present in an amount of about 0.05% to about 2% by weight based on the total weight of the formulation.

9. The formulation of claim 6, wherein the filler is microcrystalline cellulose, the glidant is silica, the extragranular glidant is silica, the binder is polyvinylpyrrolidone, the disintegrant is croscarmellose sodium, and the lubricant is magnesium stearate.

10. The formulation of claim 1, wherein:
the granules comprise:
the glidant in an amount of about 1 wt % to about 3 wt % based on the total weight of the formulation,
a binder in an amount of about 1 wt % to about 10 wt % based on the total weight of the formulation, and
a filler in an amount of about 2 wt % to about 30 wt %, and
the one or more extragranular excipients comprise one or more of:
a disintegrant in an amount of 0 wt % to about 10 wt % based on the total weight of the formulation, and
a lubricant in an amount of about 0.05 wt % to about 2 wt % based on the total weight of the formulation.

11. The formulation of claim 1, wherein the granulate formulation comprises an effective amount of the glidant and the extragranular glidant to provide a flow function coefficient of the formulation of at least about 4.

* * * * *